(12) United States Patent
Suzuki

(10) Patent No.: US 10,649,191 B2
(45) Date of Patent: May 12, 2020

(54) SPECIMEN OBSERVATION APPARATUS AND SPECIMEN OBSERVATION METHOD

(71) Applicant: OLYMPUS CORPORATION, Hachioji-shi, Tokyo (JP)

(72) Inventor: Yoshimasa Suzuki, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 222 days.

(21) Appl. No.: 15/794,877

(22) Filed: Oct. 26, 2017

(65) Prior Publication Data

US 2018/0045944 A1    Feb. 15, 2018

Related U.S. Application Data

(63) Continuation of application No. PCT/JP2015/065152, filed on May 20, 2015.

(51) Int. Cl.
*G02B 21/14* (2006.01)
*C12Q 1/02* (2006.01)
(Continued)

(52) U.S. Cl.
CPC ............ *G02B 21/14* (2013.01); *C12M 41/46* (2013.01); *C12Q 1/02* (2013.01); *G02B 21/367* (2013.01)

(58) Field of Classification Search
CPC .... G02B 21/00; G02B 21/0004; G02B 21/06; G02B 21/08; G02B 21/088; G02B 21/14;
(Continued)

(56) References Cited

U.S. PATENT DOCUMENTS

2005/0168808 A1   8/2005  Ishiwata
2007/0177255 A1   8/2007  Kanegasaki et al.
(Continued)

FOREIGN PATENT DOCUMENTS

JP        09292572 A    11/1997
JP      2004348104 A    12/2004
(Continued)

OTHER PUBLICATIONS

MetaMorph, "How to use shading correction and background subtraction," http://mdc.custhelp.com/app/answers/detail/a_id/18800/~/how-to-use-shading-correction-and-background-subtraction, published Dec. 20, 2010, accessed online Jul. 23, 2019 (Year: 2010).*
(Continued)

*Primary Examiner* — Stephone B Allen
*Assistant Examiner* — Adam W Booher
(74) *Attorney, Agent, or Firm* — Holtz, Holtz & Volek PC

(57) ABSTRACT

A specimen observation apparatus includes: a light source; an illumination optical system; a stage; an imaging optical system; and a reflection member disposed at a position opposed to the imaging optical system across the stage. The illumination optical system is disposed so as to apply illumination light from the light source to a specimen. The imaging optical system is disposed at a position at which the illumination light that is transmitted through the specimen and thereafter reflected by the reflection member to be transmitted through the specimen again enters, and is configured to form an optical image of the specimen. The optical image is formed in a state in which a position of the specimen and a focus position of the imaging optical system are different from each other.

18 Claims, 17 Drawing Sheets

(51) Int. Cl.
*C12M 1/34* (2006.01)
*G02B 21/36* (2006.01)

(58) Field of Classification Search
CPC .... G02B 21/36; G02B 21/365; G02B 21/367; G02B 21/086; G02B 21/12; C12M 41/46; C12Q 1/02
See application file for complete search history.

(56) References Cited

U.S. PATENT DOCUMENTS

| | | |
|---|---|---|
| 2009/0201580 A1 | 8/2009 | Ishiwata |
| 2016/0025959 A1 | 1/2016 | Suzuki |

FOREIGN PATENT DOCUMENTS

| | | |
|---|---|---|
| JP | 2005173288 A | 6/2005 |
| JP | 2006174764 A | 7/2006 |
| JP | 2014167587 A | 9/2014 |

OTHER PUBLICATIONS

Japanese Office Action (and English language translation thereof) dated Apr. 3, 2019 issued in counterpart Japanese Application No. 2017-518714.
International Preliminary Report on Patentability (and English translation thereof) dated Nov. 30, 2017 issued in International Application No. PCT/JP2015/065152.
International Search Report (ISR) and Written Opinion dated Aug. 25, 2015 issued in International Application No. PCT/JP2015/065152.

* cited by examiner

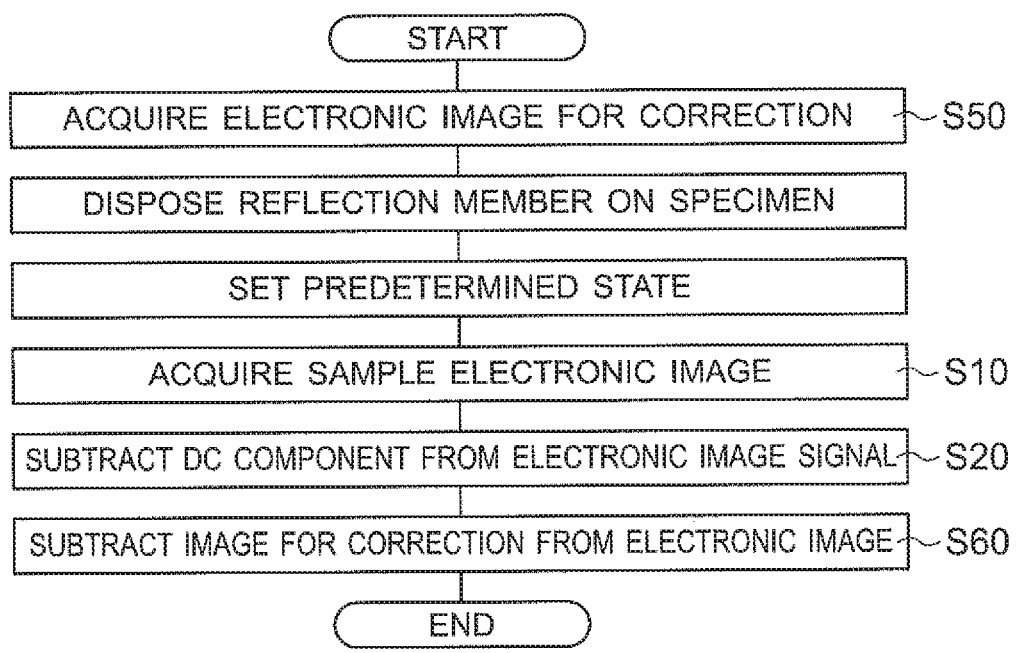

SPECIMEN OBSERVATION APPARATUS AND SPECIMEN OBSERVATION METHOD

CROSS-REFERENCE TO RELATED APPLICATION

The present application is a continuation application of International Application No. PCT/JP2015/065152 filed on May 20, 2015, the entire contents of which are incorporated herein by reference.

BACKGROUND OF THE INVENTION

Field of the Invention

The present invention relates to a specimen observation apparatus and a specimen observation method.

Description of the Related Art

In recent years, in order to elucidate the life phenomenon of living cells in the cellular level, a method of observing the behavior of the cells over time while continuing cell cultivation, that is, what is called time-lapse imaging has become widely used. In the time-lapse imaging, an observation apparatus in which an incubator and a phase contrast microscope are combined is used. However, since the observation apparatus as described above is based on observation with transmitted illumination, there has been a problem in that the apparatus is enlarged.

A compact observation apparatus that can perform observation with transmitted illumination is disclosed in Japanese Patent Application Publication No. 2004-348104. In the observation apparatus in Japanese Patent Application Publication No. 2004-348104, a reflection surface is provided on a bottom surface of observation equipment in which a specimen is stored. Then, an observation optical system is disposed so as to be opposed to the reflection surface.

In the observation apparatus in Japanese Patent Application Publication No. 2004-348104, a light source is disposed on the observation optical system side. Illumination light exited from the light source is applied to the specimen through the observation optical system. The illumination light that has been transmitted through the specimen is reflected by the reflection surface and is applied to the specimen again. As a result, the transmitted illumination is performed on the specimen. In the observation apparatus in Japanese Patent Application Publication No. 2004-348104, since there is no need to dispose a light source for illumination on the side opposed to the observation optical system across the specimen or on the condenser lens side, the observation apparatus can be downsized.

SUMMARY OF THE INVENTION

A specimen observation apparatus of the present invention includes:
a light source;
an illumination optical system;
a stage on which a specimen is able to be disposed;
an imaging optical system; and
a reflection member disposed at a position opposed to the imaging optical system across the stage, wherein
the illumination optical system is disposed so as to apply illumination light from the light source to the specimen,
the imaging optical system is disposed at a position at which the illumination light that is transmitted through the specimen and thereafter reflected by the reflection member to be transmitted through the specimen again enters, and is configured to form an optical image of the specimen,
the optical image is formed in a state in which a position of the specimen and a focus position of the imaging optical system are different from each other, and
the focus position is a position at which phases of zero-order diffracted light and first-order diffracted light at a spatial frequency of the specimen at a position of an image point on an optical axis are the same.

Moreover, a specimen observation method of the present invention includes:
an acquisition step of acquiring an electronic image of a specimen; and
a subtraction step of subtracting a direct current component from a signal of the electronic image, wherein
the acquisition step is performed in a state of bright-field observation and a state in which illumination light that is transmitted through the specimen is applied toward the specimen again,
the electronic image at the subtraction step is an image acquired in a predetermined state,
in the predetermined state, a position of the specimen and a focus position of an imaging optical system are different from each other, and
the focus position is a position at which phases of zero-order diffracted light and first-order diffracted light at a spatial frequency of the specimen at a position of an image point on an optical axis are the same.

BRIEF DESCRIPTION OF THE DRAWINGS

FIG. 16 is a flowchart of a specimen observation method of a fourth embodiment;

DETAILED DESCRIPTION OF THE INVENTION

Action and effect of embodiments according to certain aspects of the present invention will be described below. An action and effect of the present embodiment will be described specifically by describing concrete examples. However, the aspects exemplified thereof are some of the aspects included in the present invention, and there is a large number of variations in these aspects. Therefore, the present invention is not restricted to the aspects that are exemplified.

A sample observation method of an embodiment and a sample observation device of an embodiment are described below. The sample observation device and the sample observation method in the following each embodiment is used in a state of bright-field observation. In the bright-field observation of the present embodiment, a fluorescent mirror unit including an excitation filter, a dichroic mirror, and an absorption filter is not used as with fluorescent observation. Therefore, in the state of bright-field observation, when a sample is colorless and transparent, the wavelength band of light forming a sample image (hereinafter, referred to as the "imaging light" as appropriate) agrees with apart of the wavelength band of light illuminating the sample (hereinafter, referred to as the "illumination light" as appropriate), or the wavelength band of the imaging light agrees with the wavelength band of the illumination light.

Moreover, in the bright-field observation of the sample observation device and the sample observation method of the present embodiment, a phase film in phase-contrast observation or a differential interference prism in differential interference observation is not used. Moreover, in the bright-field observation of the present embodiment, a modulator in the modulation contrast observation is not used.

A specimen observation apparatus of the present embodiment includes: a light source; an illumination optical system; a stage on which a specimen is able to be disposed; an imaging optical system; and a reflection member disposed at a position opposed to the imaging optical system across the stage. The illumination optical system is disposed so as to apply illumination light from the light source to the specimen, the imaging optical system is disposed at a position at which the illumination light that is transmitted through the specimen and thereafter reflected by the reflection member to be transmitted through the specimen again enters, and is configured to form an optical image of the specimen. The optical image is formed in a state in which a position of the specimen and a focus position of the imaging optical system are different from each other. The focus position is a position at which phases of zero-order diffracted light and first-order diffracted light at a spatial frequency of the specimen at a position of an image point on an optical axis are the same.

Figure 1:
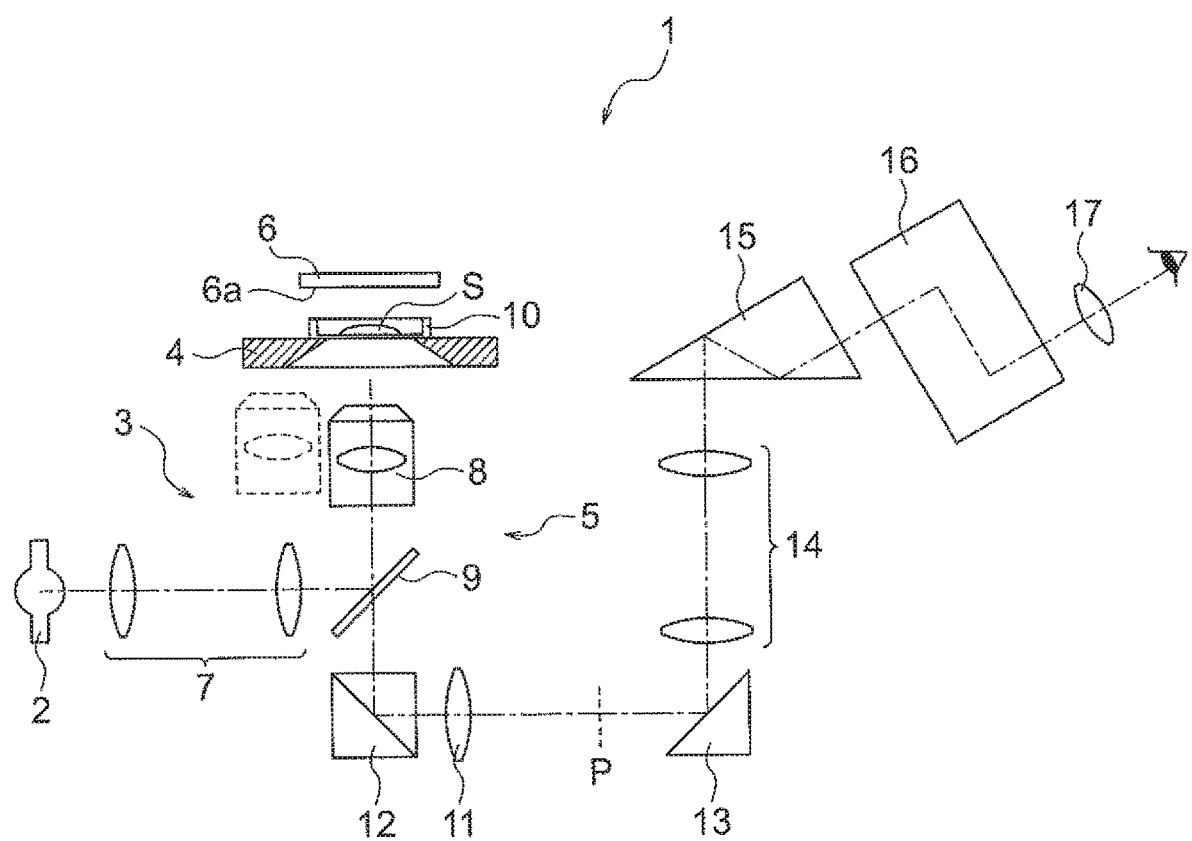
FIG. 1 is a diagram illustrating the configuration of a specimen observation apparatus of a first embodiment.

A specimen observation apparatus of a first embodiment and a specimen observation apparatus of a second embodiment are described below. The specimen observation apparatus of the first embodiment and the specimen observation apparatus of the second embodiment both have a basic configuration of the specimen observation apparatus of the present embodiment (hereinafter referred to as "basic configuration"). The basic configuration is described here with use of the specimen observation apparatus of the first embodiment. FIG. 1 is a diagram illustrating the configuration of the specimen observation apparatus of the first embodiment.

A specimen observation apparatus 1 of the first embodiment is an apparatus using an inverted microscope, for example. The specimen observation apparatus 1 includes, as the basic configuration, a light source 2, an illumination optical system 3, a stage 4, an imaging optical system 5, and a reflection member 6.

The light source 2 is located below the stage 4 in the figure. Illumination light is emitted from the light source 2. For the light source 2, for example, a halogen lamp, a xenon lamp, a mercury lamp, a laser, or a light emitting diode is used.

The illumination light emitted from the light source 2 enters the illumination optical system 3. The illumination optical system 3 is located below the stage 4 in the figure. The illumination optical system 3 is configured by a light collecting optical system 7 and an objective lens 8. As described later, the objective lens 8 forms the imaging optical system 5 together with a tube lens 11. In this manner, the objective lens 8 is used in common with the illumination optical system 3 and the imaging optical system 5.

In FIG. 1, the light collecting optical system 7 is configured by two lenses, but the number of the lenses is not limited to two. Moreover, the light collecting optical system 7 may include an optical filter or an aperture stop.

The illumination light passes through the light collecting optical system 7 and enters a half mirror 9. Then, the illumination light is reflected by the half mirror 9 and enters the objective lens 8. The illumination light that has passed through the objective lens 8 reaches the stage 4.

The illumination light passes through an opening portion formed in the stage 4. A specimen S held in a container 10 is placed above the opening portion in the stage 4. Therefore, the illumination light is applied to the specimen S through the opening portion in the stage 4. When the specimen S is colorless and transparent, the illumination light applied to the specimen S is transmitted through the specimen S. The illumination light transmitted through the specimen S enters the reflection member 6.

The reflection member 6 is disposed above the stage 4 in the figure. In this case, the light source 2 and the imaging optical system 5 are disposed on the illumination optical system 3 side. Therefore, the reflection member 6 is disposed at a position opposed to the imaging optical system 5 across the stage 4. The reflection member 6 is, for example, a parallel plate having a surface on which a reflection film 6a is formed.

The reflection member 6 is disposed above the specimen S. Then, the reflection member 6 is disposed such that the surface on which the reflection film 6a is formed faces the stage 4. The illumination light transmitted through the specimen S is reflected by the reflection member 6, and the reflected illumination light is applied to the specimen S again. As a result, transmitted illumination is performed on the specimen S.

In this way, in the basic configuration, the transmitted illumination can be performed on the specimen S similarly to transmitted illumination in the conventional microscopes.

Light from the specimen S enters the imaging optical system 5. The imaging optical system 5 is configured by the objective lens 8 and the tube lens 11. The light from the specimen S passes through the objective lens 8 and the half mirror 9 and is condensed by the tube lens 11.

When the objective lens 8 is disposed at the position indicated by the broken line, the position of the specimen S is aligned with the focus position of the imaging optical system 5. In this case, an image of the specimen S is clearly formed at a position P at which light is condensed by the tube lens 11. That is, an in-focus image of the specimen S is formed at the position P.

When the specimen S is colorless and transparent, for example, a living cell, the specimen S has no contrast. Therefore, in the state in which the position of the specimen S is aligned with the focus position of the imaging optical system 5, the image of the specimen S formed at the position P has no contrast. Therefore, the specimen S cannot be observed.

Thus, in the specimen observation apparatus 1, in the above-mentioned basic configuration, the image of the specimen S is formed in a state in which the position of the specimen S and the focus position of the imaging optical system 5 (hereinafter referred to as "focus position") are different from each other.

In order to make the position of the specimen S and the focus position different from each other, for example, the objective lens 8 only needs to be moved to a position conceived to be misaligned with the focus position through eye measurement. Alternatively, the focus position and the position of the specimen S may be first aligned with each other, and then the objective lens 8 may be moved in a direction away from the focus position. Alternatively, when the focus position is known in advance, the position misaligned with the focus position can be determined in advance, and hence the objective lens 8 only needs to be moved to that position.

When the stage 4 is movable, the stage 4 may be moved. Moreover, both the objective lens 8 and the stage 4 may be moved.

In FIG. 1, the objective lens 8 is indicated by the broken line and the solid line. The position indicated by the broken line is a position of the objective lens 8 when the position of the specimen S and the focus position are aligned with each other. The position indicated by the solid line is a position of the objective lens 8 when the position of the specimen S and the focus position are different from each other.

In this manner, the objective lens 8 is moved from the position indicated by the broken line to the position indicated by the solid line, and the position of the specimen S and the focus position are made different from each other. In FIG. 1, the difference between the position indicated by the solid line and the position indicated by the broken line is exaggerated such that the movement of the objective lens 8 can be seen, but the actual amount of movement is small. Moreover, the direction in which the objective lens 8 is moved may be either of a direction approaching the stage 4 or a direction away from the stage 4.

When the specimen S is a lattice phase object, non-diffracted light (hereinafter referred to as "zero-order diffracted light") and diffracted light are generated from the specimen S when the specimen S is illuminated with a parallel light flux. In the microscope, the image of the specimen S is formed through the composition of the zero-order diffracted light and the diffracted light.

Since intensity of light is observed at the image plane, the intensity I of light at the image plane can be represented by the following expression:

$$I = |E|^2 = A_2^2 + 2A_1 A_2 \cos \psi,$$

where $A_1$ denotes an amplitude of zero-order diffracted light, $A_2$ denotes an amplitude of diffracted light, $\phi 1(r)$ denotes a phase of zero-order diffracted light, and $\phi 2(r)$ denotes a phase of diffracted light, and $\psi$ denotes a phase difference, and $\psi = \phi 1(r) - \phi 2(r)$.

In the following description, an image (optical image) of a sample S is assumed to be formed by zero-order diffracted light and first-order diffracted light.

Taking notice of the point where the sample S and the optical axis intersect (one point on the optical axis), since zero-order diffracted light is not diffracted, zero-order diffracted light emanated from this point travels along the optical axis and reaches the center of the pupil.

On the other hand, since first-order diffracted light is diffracted in a predetermined direction, the first-order diffracted light emanated from this point is incident on the image forming optical system 5 at a predetermined angle with respect to the optical axis. The first-order diffracted light incident on the image forming optical system 5 reaches a position away from the center of the pupil plane.

Here, an in-focus state is a state in which the position of the specimen S is aligned with the focus position and a defocused state is a state in which the position of the specimen S is misaligned with the focus position. The focus position is a position at which a phase of the zero-order diffracted light at the spatial frequency of the specimen S and a phase of the first-order diffracted light at the spatial frequency of the specimen S are the same at the position of the image point on the optical axis.

In the in-focus state, an amount of wavefront aberration is 0 at any place on the pupil plane. This indicates that the amount of wavefront aberration in zero-order diffracted light and the amount of wavefront aberration in first-order diffracted light are both 0. Since a value obtained by multiplying the amount of wavefront aberration by $(2\pi/\lambda)$ is equivalent to the phase amount, at a time of in-focusing, a change in phase does not arise for both of the zero-order diffracted light and the first-order diffracted light.

In this case, since the phase of the first-order diffracted light remains to be delayed relative to the phase of the zero-order diffracted light by $\pi/2$, the phase difference is expressed by $\psi = 0 - (-\pi/2) = \pi/2$. In this case, since $2A_1 A_2 \cos \psi = 0$, phase information cannot be obtained in the form of contrast information. As a result, the electronic image becomes an image without contrast.

On the other hand, in the defocus state, although the amount of wavefront aberration is 0 at the center of the pupil plane, the wavefront aberration occurs at a position away from the center of the pupil. Here, the wavefront aberration is a displacement of actual wavefront with reference to a reference wavefront, and this displacement is a displacement in phase. Therefore, if the first-order diffracted light is positioned in the range where wavefront aberration occurs, the phase of the first-order diffracted light is equivalent to a phase that the amount of wavefront aberration is added to the original phase of the first-order diffracted light. As just described, by displacing the position of the sample S from the in-focus position, it is possible to change the phase of the first-order diffracted light.

Thus, the amount of wavefront aberration at the first-order diffracted light is made to be $-\lambda/4$ while keeping the amount of wavefront aberration at the zero-order diffracted light 0. As described above, since the value obtained by multiplying the amount of wavefront aberration by $(2\pi/\lambda)$ equals the phase amount, at a time of defocusing, a change in phase does not arise for the zero-order diffracted light, but a change in phase arise for the first-order diffracted light. Specifically, in the first-order diffracted light, the phase further delays by $\lambda/4\times(2\pi/\lambda)=\pi/2$ in addition to the original phase delay of $\pi/2$. Since the phase of the first-order diffracted light delays by $\pi$ relative to the phase of the zero-order diffracted light, the phase difference is expressed by $\psi=0-(-\pi)=\pi$. In this case, since $2A_1A_2 \cos \psi \neq 0$, phase information can be obtained in the form of contrast information. As a result, an optical image of the sample S becomes an image with obvious contrast. Therefore, an observer can observe the sample S (image of the sample S) clearly.

In this manner, in the basic configuration, an optical image is formed in the state in which the position of the specimen S and the focus position are different from each other, and hence an optical image having a contrast is formed. Therefore, the distance between the specimen S and the reflection member 6 is not limited in the basic configuration.

Moreover, as described above, in the basic configuration, the transmitted illumination can be performed on the specimen similarly to the conventional microscopes. However, in the basic configuration, only the reflection member 6 is disposed at a position opposed to the imaging optical system 5 across the stage 4. That is, a light source or an optical system for transmitted illumination is not disposed at the position opposed to the imaging optical system 5 across the stage 4.

Based on this, according to the basic configuration, a colorless and transparent specimen can be observed without limitation in thickness thereof even in the state of bright-field observation, and the apparatus can be downsized.

Examples of methods of observing the specimen S include a method of observing the optical image directly by sight and a method of converting the optical image into an electronic image and observing the electronic image.

In the specimen observation apparatus of the first embodiment, the optical image can be observed directly by sight. Therefore, the specimen observation apparatus of the first embodiment includes a prism 12, a prism 13, a relay optical system 14, a prism 15, a binocular splitting prism 16, and an eyepiece 17 in addition to the above-mentioned basic configuration.

Light from the specimen S passes through the objective lens 8 and the half mirror 9 and enters the prism 12. Light reflected by the prism 12 is condensed by the tube lens 11.

In the state in which the position of the specimen S and the focus position are different from each other, an optical image having a contrast is formed at the position P. Light from the optical image of the specimen S is reflected by a mirror surface of the prism 13 and passes through the relay optical system 14 and the prism 15, and then enters the binocular splitting prism 16. An optical path for the right eye and an optical path for the left eye are formed by the binocular splitting prism 16. The eyepiece 17 is disposed in each of the optical path for the right eye and the optical path for the left eye.

The image of the specimen S is relayed by the relay optical system 14, and the relayed image of the specimen S is formed in the vicinity of the eyepiece 17. As a result, an observer can observe the image of the specimen S by both eyes.

It is preferred that the specimen observation apparatus of the present embodiment include an image pickup device and an image processing device, the image pickup device be disposed at a position at which the optical image is formed, and the image processing device generate an observation image signal from the optical image obtained in the state in which the position of the specimen and the focus position of the imaging optical system are different from each other.

Figure 2:
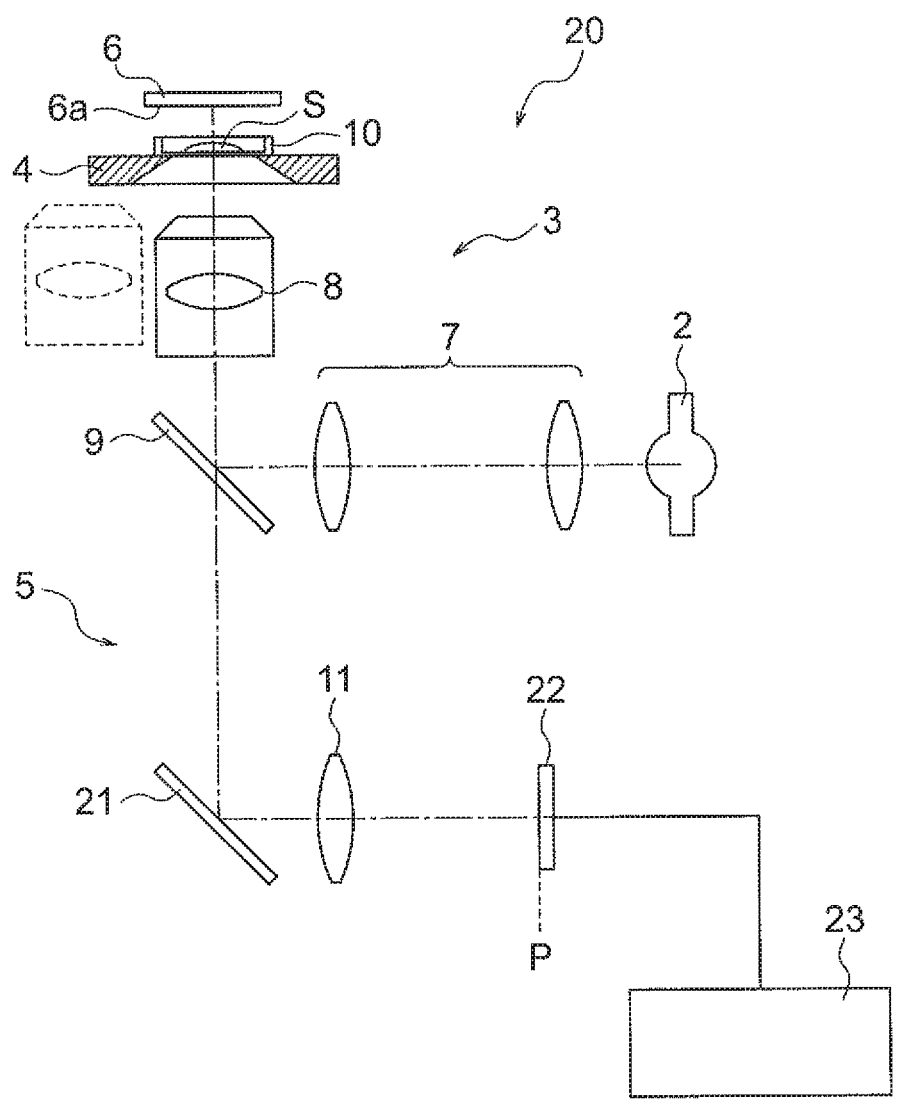
FIG. 2 is a diagram illustrating the configuration of a specimen observation apparatus of a second embodiment.

FIG. 2 is a diagram illustrating the configuration of a specimen observation apparatus of the second embodiment. The same configuration as in FIG. 1 is denoted by the same number and its detailed description is omitted.

In the specimen observation apparatus of the second embodiment, an optical image of a specimen can be converted into an electronic image and observed. Therefore, a specimen observation apparatus 20 includes a mirror 21, an image pickup device 22, and an image processing device 23 in addition to the above-mentioned basic configuration.

Light from the specimen S passes through the objective lens 8 and the half mirror 9 and enters the mirror 21. Light reflected by the mirror 21 is condensed by the tube lens 11.

In the state in which the position of the specimen S and the focus position are different from each other, an optical image having a contrast is formed at the position P. Since the image pickup device 22 is disposed at the position P, the image of the specimen S is picked up by the image pickup device 22. A CCD or a CMOS is used as the image pickup device 22, for example. Image data of the specimen S is acquired by the image pickup device 22. The acquired image data of the specimen S is sent to the image processing device 23.

In the image processing device 23, various kinds of processing are performed with use of the image data of the specimen S and an observation image signal is generated. Here, the image data of the specimen S is acquired in the state in which the position of the specimen S and the focus position of the imaging optical system are different from each other. Therefore, in the image processing device 23, the observation image signal is generated from the optical image acquired in the state in which the position of the specimen and the focus position of the imaging optical system are different from each other.

Figure 3:
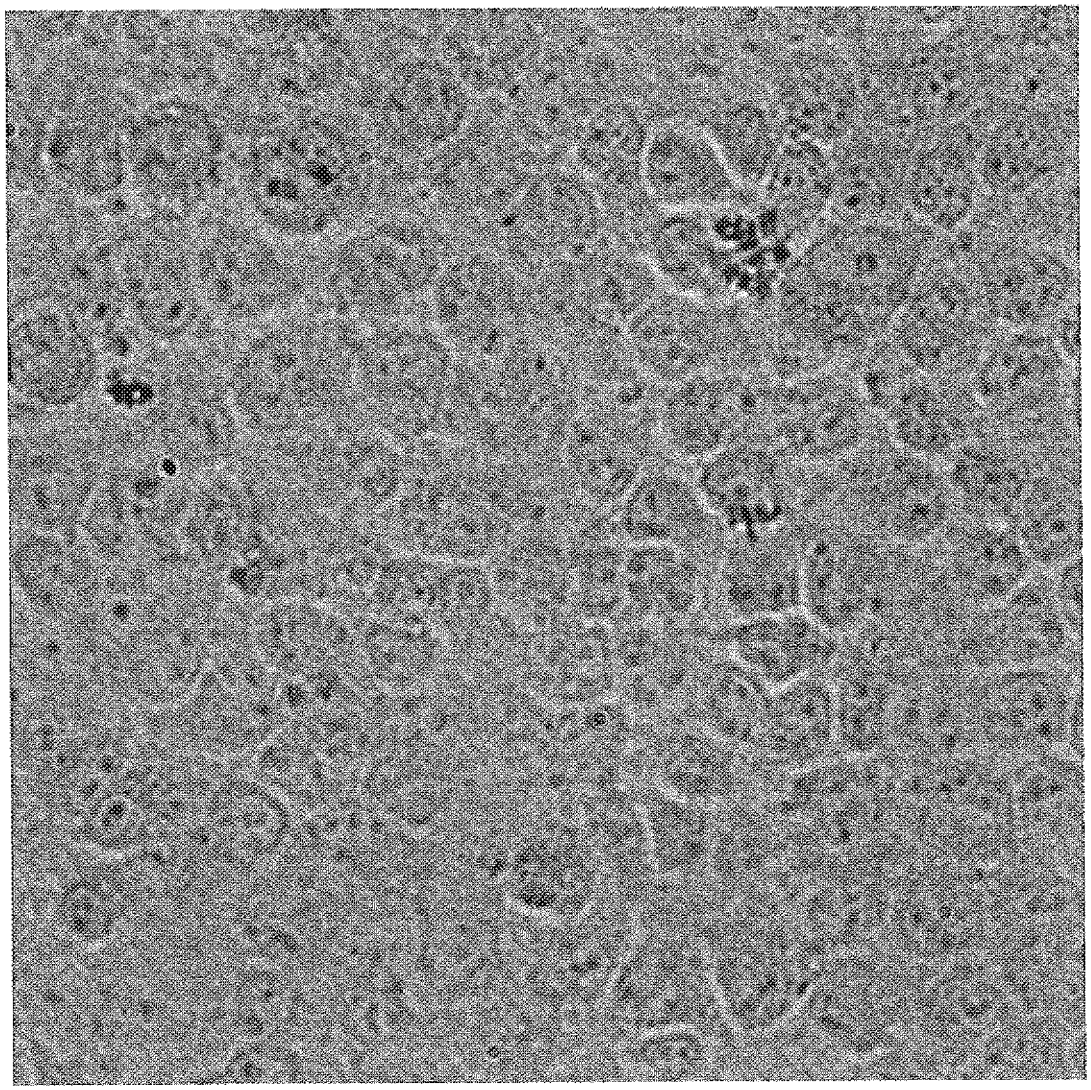
FIG. 3 is an electronic image of a specimen obtained by the specimen observation apparatus of the present embodiment that is an electronic image before enhancement.
Figure 4:
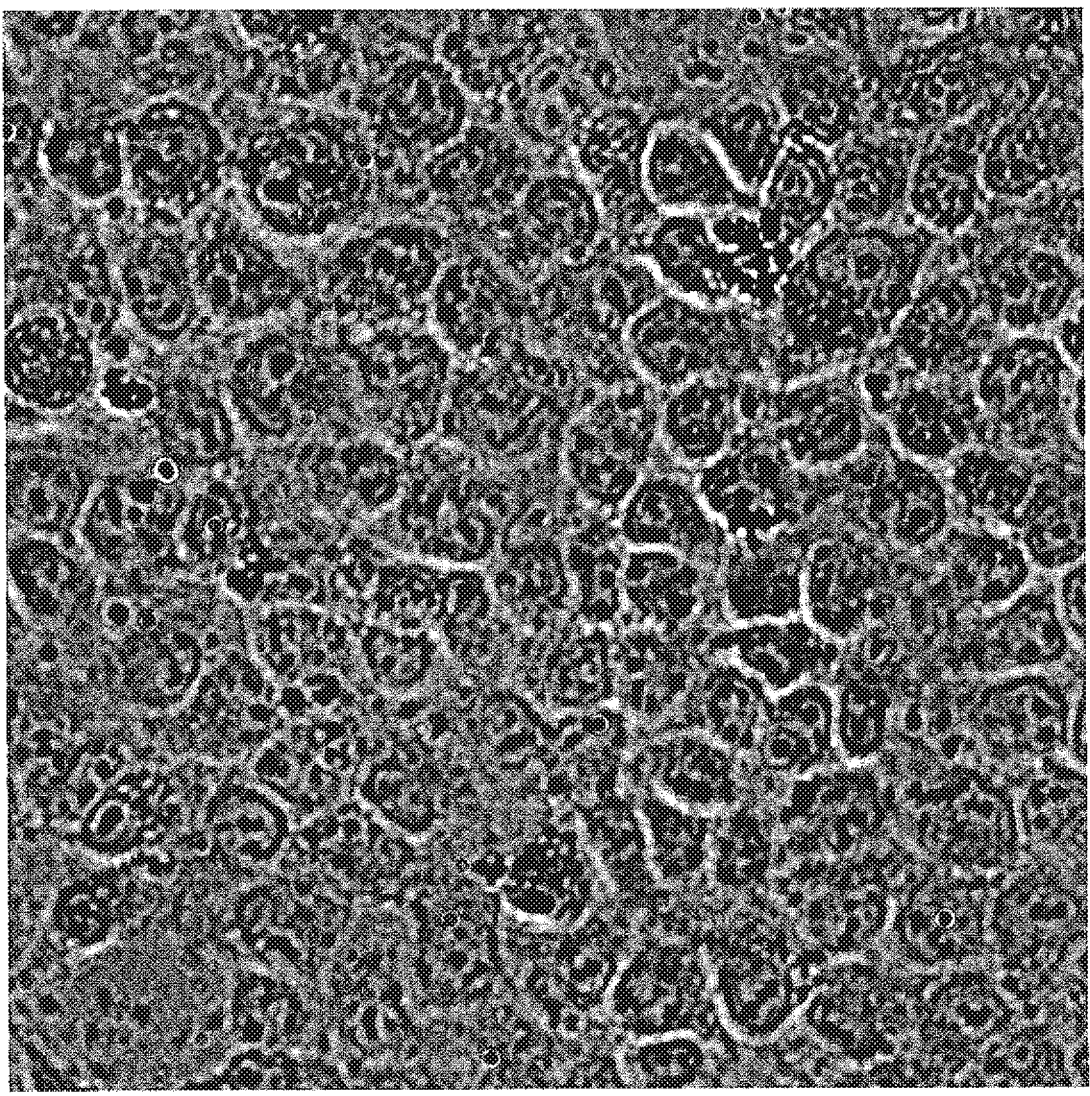
FIG. 4 is an electronic image of the specimen obtained by the specimen observation apparatus of the present embodiment that is an electronic image after enhancement.

The electronic image of the specimen obtained by the specimen observation apparatus of the second embodiment is illustrated in FIG. 3 and FIG. 4. FIG. 3 is an electronic image before enhancement and FIG. 4 is an electronic image after enhancement. A 10× objective lens is used to acquire the electronic image. Moreover, the numerical aperture of the objective lens ($NA_{ob}$) is 0.25, the numerical aperture of the illumination light ($NA_{ill}$) is 0.13, the wavelength ($\lambda$) is 550 nm, and the misalignment amount from the focus position is 10 μm. Moreover, a distance between the position of the specimen and a reflection surface of the reflection member (D) is 12 mm.

As described above, in the specimen observation apparatus of the first embodiment and the specimen observation apparatus of the second embodiment (hereinafter referred to as "specimen observation apparatus of the present embodiment"), the reflection member is used. The configuration of the reflection member is described.

Figure 5:
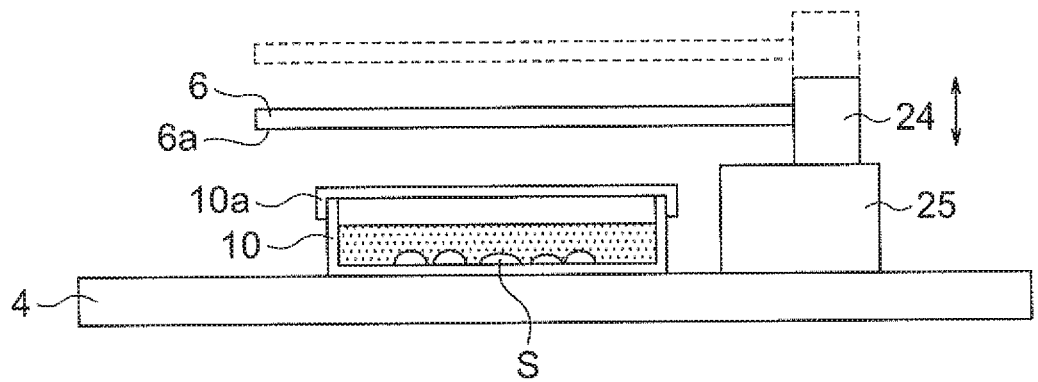
FIG. 5 is a diagram illustrating a configuration example of a reflection member.

The configuration example of the reflection member is illustrated in FIG. 5. The reflection member 6 is held by a first holding member 24. The first holding member 24 is held by a second holding member 25. The second holding member 25 is fixed on the stage 4.

The first holding member 24 is movable in the upward direction in the figure with respect to the second holding member 25. Therefore, the distance between the reflection member 6 and the specimen S can be adjusted by moving the first holding member 24.

Moreover, the container 10 may have a lid 10a.

Figure 6:
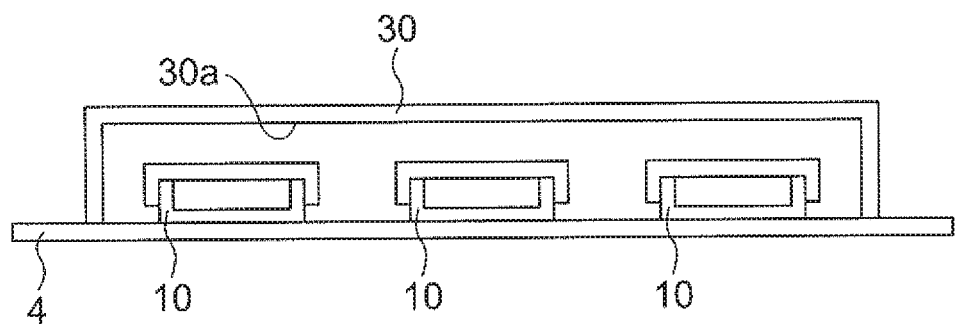
FIG. 6 is a diagram illustrating another configuration example of a reflection member.

Another configuration example of the reflection member is illustrated in FIG. 6. A reflection member 30 is a box-shaped member and is placed on the stage 4 so as to cover containers 10. A reflection film 30a is formed on the inner surface of a recessed portion. The recessed portion has a size that covers at least one container 10. In FIG. 6, the recessed portion has a size that covers three containers 10.

Figure 7:
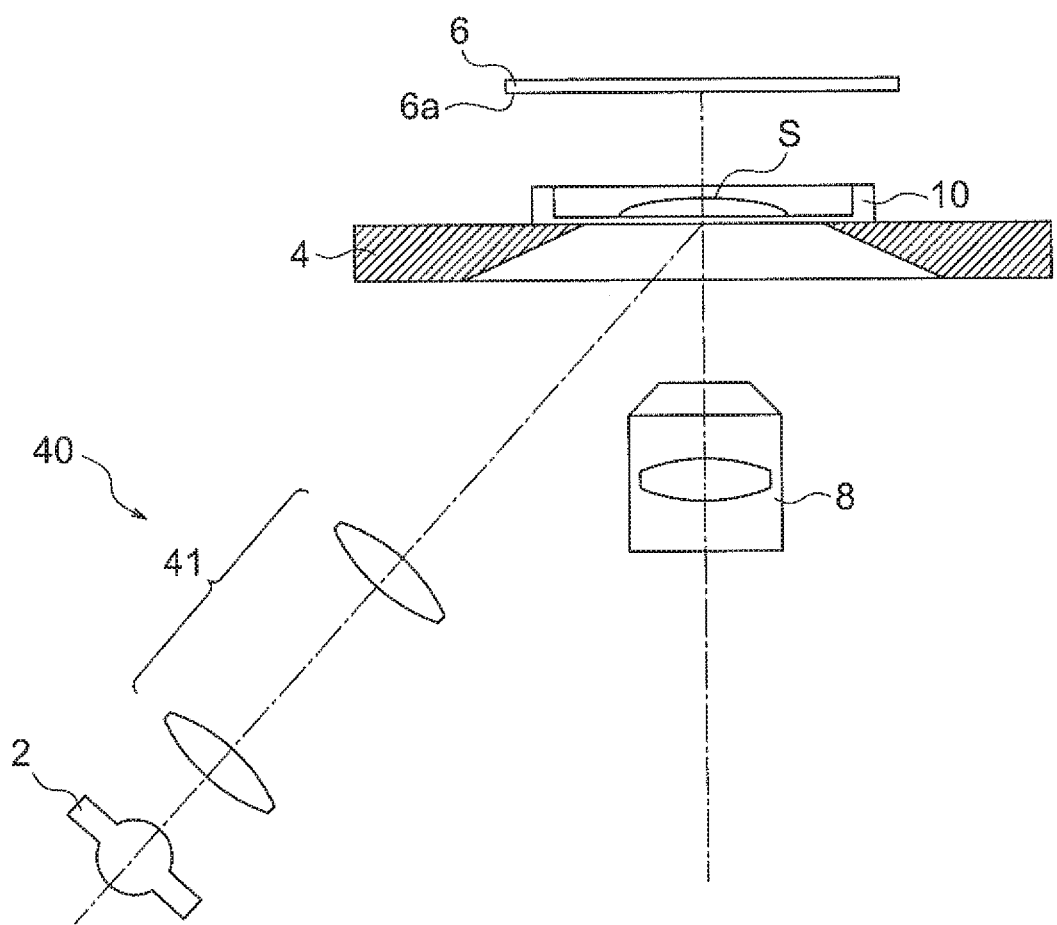
FIG. 7 is a diagram illustrating another illumination method.

In the specimen observation apparatus 1 and the specimen observation apparatus 20, illumination light is applied to the specimen S through the objective lens 8. However, the illumination light may be applied to the specimen S without passing through the objective lens 8. FIG. 7 is a diagram illustrating another illumination method.

In another illumination method, an illumination optical system 40 includes the light source 2 and a light collecting optical system 41. The illumination optical system 40 is disposed such that the optical axis of the illumination optical system 40 intersects with the optical axis of the objective lens 8 (imaging optical system) at the position of the specimen S.

When the illumination light is applied to the specimen S through the objective lens 8, the illumination light and the light from the specimen S (light that forms the optical image of the specimen S) are both reduced by the half mirror 9. Meanwhile, in the illumination optical system 40, neither of the illumination light or the light from the specimen S is reduced.

In the specimen observation apparatus of the present embodiment, it is preferred that the following Conditional Expression (1) be satisfied:

$$10 \leq D \times NA_{ob}^2/\lambda \leq 10000 \quad (1)$$

where

D is a distance (mm) between the position of the specimen and the reflection surface of the reflection member;

$NA_{ob}$ is a numerical aperture of the imaging optical system on the specimen side; and $\lambda$ is a center wavelength (mm) of a wavelength range of the illumination light.

In case of falling below a lower limit value of Conditional Expression (1), the reflection member 6 becomes too close to the specimen S. Therefore, when there is dirt or dust on the reflection member 6, an image thereof overlaps with the image of the specimen S. Moreover, the possibility of the specimen S being damaged by heat of the reflection member 6 increases.

In case of exceeding an upper limit value of Conditional Expression (1), the reflection member 6 becomes too far away from the specimen S. In this case, the apparatus is upsized. Moreover, the optical loss of the illumination light increases.

It is preferred that the following Conditional Expression (1') be satisfied instead of Conditional Expression (1).

$$20 \leq D \times NA_{ob}^2/\lambda \leq 5000 \quad (1')$$

It is further preferred that the following Conditional Expression (1") be satisfied instead of Conditional Expression (1).

$$40 \leq D \times NA_{ob}^2 8\lambda \leq 2500 \quad (1'')$$

Moreover, a preferred upper limit value of D is 40 mm or 20 mm. A preferred lower limit value of D is 1 mm, 2 mm, or 4 mm.

Moreover, in the specimen observation apparatus of the present embodiment, it is preferred that the following Conditional Expression (2) be satisfied:

$$4 \times NA_{ill} \times D + A < L \quad (2)$$

where $NA_{ill}$ is a numerical aperture of the illumination optical system on the specimen side;

D is the distance (mm) between the position of the specimen and the reflection surface of the reflection member;

A is a diameter (mm) of an observation field of view at the position of the specimen;

L is a diameter (mm) of an illumination range of the illumination optical system at the position of the specimen; and the diameter of the observation field of view and the diameter of the illumination range are diameters in the state in which the position of the specimen and the focus position of the imaging optical system are different from each other.

By satisfying Conditional Expression (2), the observation range can be illuminated with the illumination light having the same numerical aperture. The contrast of the optical image depends on the numerical aperture of the illumination light. Therefore, when the observation range can be illuminated with the illumination light having the same numerical aperture, the variation of contrast in the images at positions in the observation range can be reduced.

Figure 8:
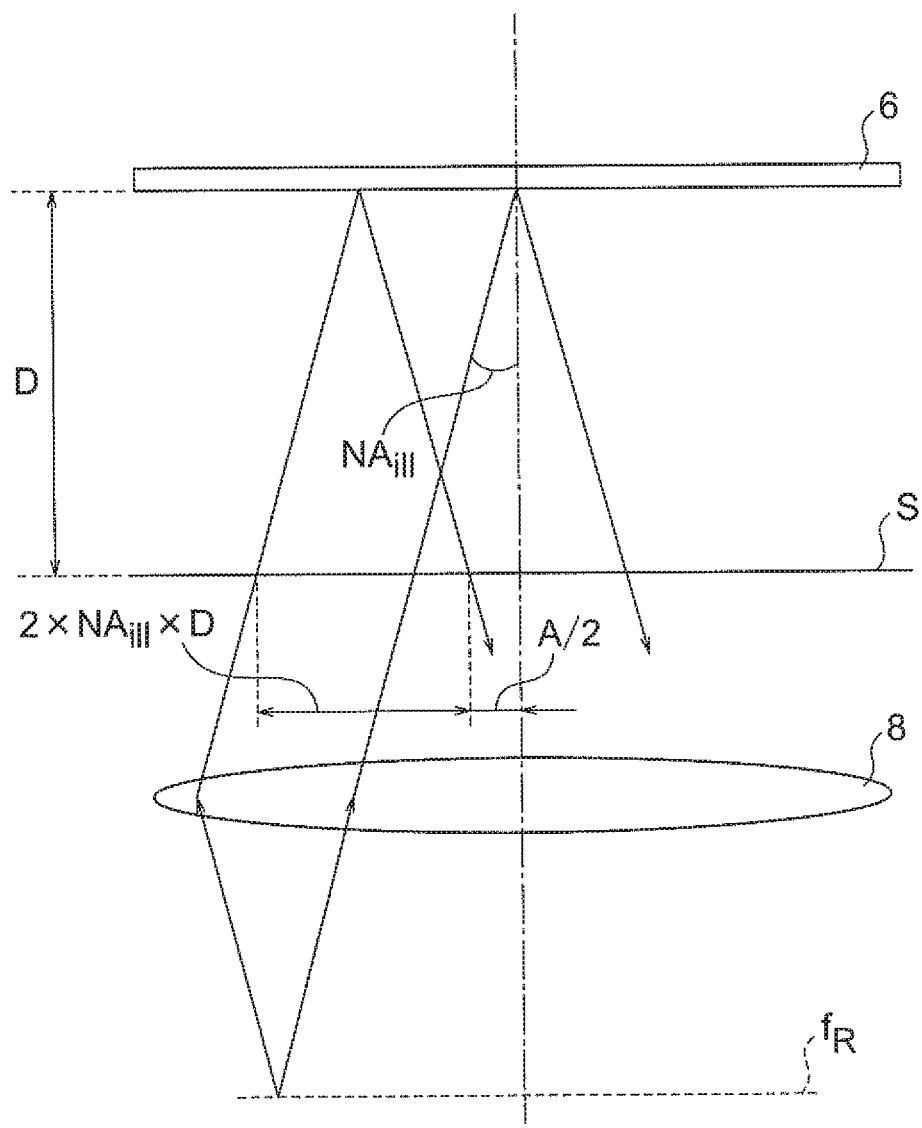
FIG. 8 is a diagram illustrating $NA_{ill}$, D, and A.

$NA_{ill}$, D, and A are illustrated in FIG. 8. As described above, the diameter of the observation field of view and the diameter of the illumination range are diameters in the state in which the position of the specimen and the focus position of the imaging optical system are different from each other. Therefore, the position of the objective lens 8 illustrated in FIG. 8 is a position in the state in which the position of the specimen and the focus position of the imaging optical system are different from each other. A rear focus position $f_R$ of the objective lens 8 (pupil position of the objective lens 8) is also a position in the state in which the position of the specimen and the focus position of the imaging optical system are different from each other. The image of the light source is formed at the position $f_R$.

When the entire field of view of the imaging optical system 5 is illuminated with the illumination light having the same numerical aperture, the observation field of view is aligned with the entire field of view of the imaging optical system 5. Therefore, the observation only needs to be performed by observing the image of the entire field of view through the eyepiece or picking up the image of the entire field of view by the image pickup device 22 and using the image of the entire field of view.

On the other hand, when a part of the region of the field of view of the imaging optical system 5 is illuminated with the illumination light having the same numerical aperture, this part of the region is the observation field of view. Thus, the observation only needs to be performed by picking up the image of the entire field of view by the image pickup device 22 and using only the image corresponding to this part of the region, that is, the image of the region satisfying Conditional Expression (2).

Moreover, in the specimen observation apparatus of the present embodiment, it is preferred that the reflection member be disposed at a position different from a position conjugate to a pupil of the imaging optical system.

As a method of reflecting the illumination light that has passed through the specimen S and applying the illumination light to the specimen S again, there is a method of disposing a lens between the specimen S and the reflection member 6. In this method, it is preferred that a front focus position of the lens and the position of the specimen S be aligned with each other and the rear focus position of the lens be aligned with the reflection member 6. By doing this, the reflection member 6 is conjugate to the pupil of the imaging optical system 5 (pupil of the objective lens 8). Therefore, the illumination light that has been reflected by the reflection member 6 is applied to the specimen in the same way as the illumination light that has passed through the specimen S first. However, the apparatus is upsized by this method.

Thus, when the reflection member is disposed at the position different from the position conjugate to the pupil of the imaging optical system, the lens becomes unnecessary and hence the apparatus can be downsized. That is, the apparatus can be downsized because only the reflection member 6 is disposed on the side opposed to the imaging optical system 5 across the stage 4.

Moreover, in the specimen observation apparatus of the present embodiment, it is preferred that the reflection member have a positive refractive power.

Figure 9A:
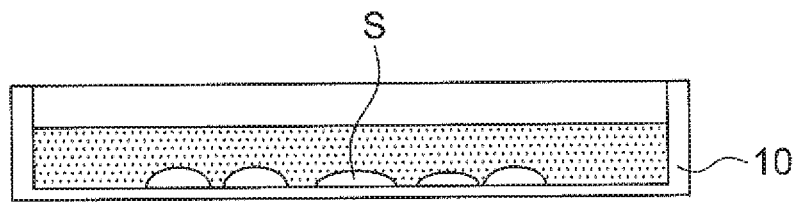
FIG. 9A is a diagram illustrating a petri dish.
Figure 9B:
FIG. 9B is a diagram illustrating a microplate.
Figure 9C:
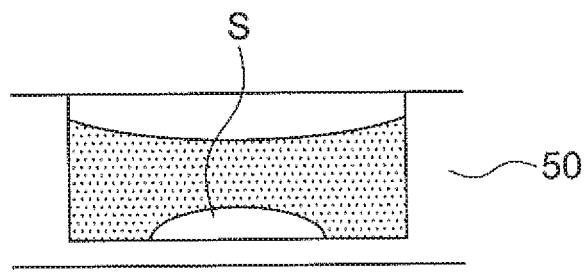
FIG. 9C is a diagram illustrating one well of a microplate.

As described above, the specimen S is held in the container 10. When the specimen S is a living cell, the cell is held in the container 10 together with liquid such as broth. As the container 10, there are a petri dish and a microplate. FIG. 9A is a diagram illustrating the petri dish. FIG. 9B is a diagram illustrating the microplate. FIG. 9C is a diagram illustrating one well of a microplate.

As illustrated in FIG. 9A, a petri dish 10 has one recessed portion, and the cell and the liquid are held in the recessed portion. In the petri dish 10, the area of the recessed portion is large, and hence the liquid level is even at most positions in the recessed portion.

Meanwhile, as illustrated in FIG. 9B, a microplate 50 has a plurality of recessed portions. In addition, as illustrated in FIG. 9C, in the microplate 50, since the area of the recessed portion is narrow, the liquid level in one well of a microplate has a concave shape. Therefore, when the liquid portion (hereinafter referred to as "medium") is considered as a lens, the medium has a function as a negative lens. When the medium has a function as a negative lens, the angle of the light beam exiting from the medium is different from the angle of the light beam entering the medium.

Figure 10A:
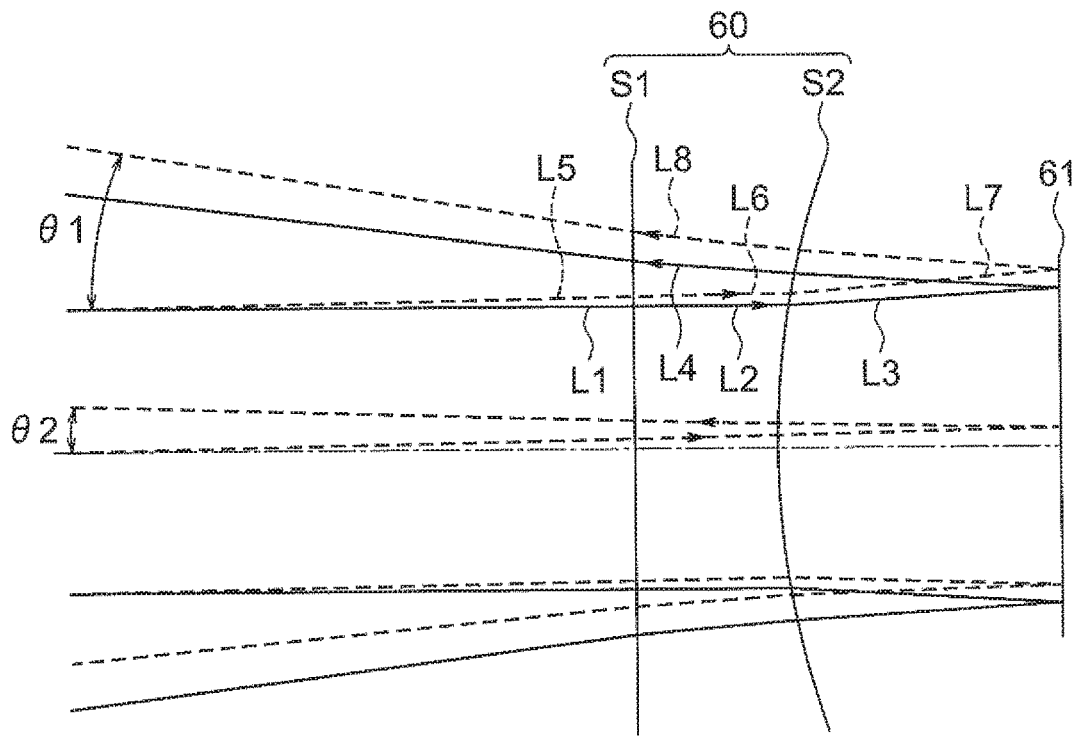
FIG. 10A is a diagram illustrating how light beams pass through a culture medium when the reflection member has a flat surface.
Figure 10B:
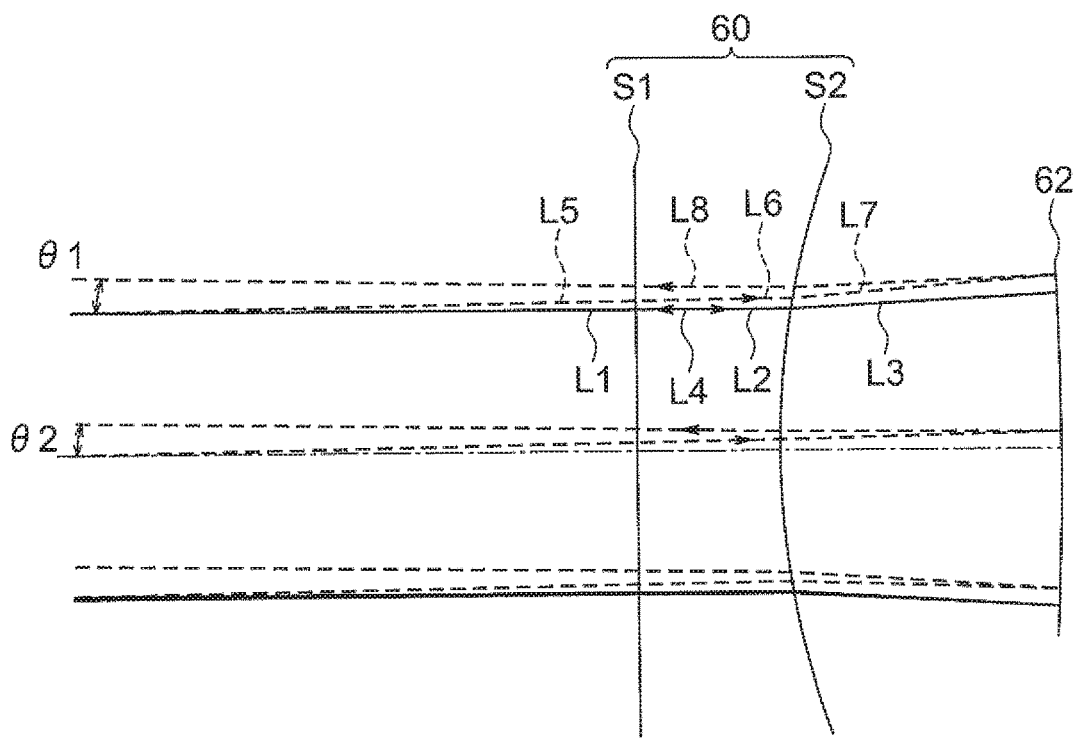
FIG. 10B is a diagram illustrating how light beams pass through the culture medium when the reflection member has a positive refractive power.

FIG. 10A is a diagram illustrating how light beams pass through the medium from the objective lens side and how light beams pass through the medium from the reflection member side when the reflection member has a flat surface. FIG. 10B is a diagram illustrating how light beams pass through the medium from the objective lens side and how light beams pass through the medium from the reflection member side when the reflection member has a positive refractive power.

Light beams having various angles are included in the illumination light. In FIG. 10A and FIG. 10B, among the light beams passing through the medium from the objective lens side, the light beam parallel to the optical axis is indicated by the solid line and the light beam intersecting with the optical axis is indicated by the broken line. Moreover, out of two surfaces of a medium 60, a surface S1 is the surface on the objective lens side and a surface S2 is the surface on the reflection member side.

The case in which the reflection member has a flat surface is described. As illustrated in FIG. 10A, a light beam L1 is a light beam entering the medium 60 from the objective lens side and is a light beam parallel to the optical axis. Since the surface S1 is a flat surface, the light beam L1 enters the inside of the medium 60 without being refracted by the surface S1. Therefore, a light beam L2 passing through the medium 60 also becomes a light beam parallel to the optical axis.

The light beam L2 passes through the surface S2 and exits from the medium 60. Since the surface S2 is a concave surface, the light beam L2 is refracted by the surface S2. As a result, a light beam L3 exits from the medium 60 in a direction away from the optical axis.

The light beam L3 enters a reflection member 61 and is reflected by the reflection surface. Since the reflection surface of the reflection member 61 is a flat surface, the light flux reflected by the reflection surface is exited in a direction further away from the optical axis. The light beam L3 reflected by the reflection surface is refracted by the surface S2 and becomes a light beam L4 that passes through the medium 60.

The light beam L2 is a light beam parallel to the optical axis, but the light beam L4 is a light beam intersecting with the optical axis. Therefore, the light beam L4 is not aligned with the light beam L2. Furthermore, the light beam L4 is exited in a direction away from the optical axis.

Next, a light beam L5 is a light beam entering the medium 60 from the objective lens side and is a light beam intersecting with the optical axis. The surface S1 is a flat surface, but the light beam L5 does not vertically enter the surface S1. Therefore, the light beam L5 is refracted by the surface S1 and enters the inside of the medium 60. A light beam L6 passing through the medium 60 also becomes a light beam intersecting with the optical axis.

The light beam L6 passes through the surface S2 and exits from the medium 60. Since the surface S2 is a concave surface, the light beam L6 is refracted by the surface S2. As a result, a light beam L7 exits from the medium 60 in a direction away from the optical axis.

The light beam L7 enters the reflection member 61 and is reflected by the reflection surface. Since the reflection surface of the reflection member 61 is a flat surface, the light flux reflected by the reflection surface exits in a direction further away from the optical axis. The light beam L7 reflected by the reflection surface is refracted by the surface S2 and becomes a light beam L8 that passes through the medium 60.

The light beam L6 and the light beam L8 are both light beams intersecting with the optical axis. However, the angle formed by the light beam L8 and the optical axis is greatly larger than the angle formed by the light beam L6 and the optical axis. Therefore, the light beam L8 and the light beam L6 are not aligned with each other. Moreover, the light beam L8 exits in a direction away from the optical axis.

In this way, when the reflection member has a flat surface, the illumination light reflected by the reflection member travels to the specimen S with the width wider than that at the time of entering the reflection member. Therefore, the illumination efficiency decreases.

Meanwhile, in the specimen observation apparatus of the present embodiment, the reflection member has a positive refractive power. A case in which the reflection member has a positive refractive power is described. As illustrated in FIG. 10B, the reflection surface of a reflection member 62 has a curved surface. Also in this case, the light beam L3 enters the reflection member 62 and is reflected by the reflection surface. However, the reflection surface of the reflection member 62 has a positive refractive power. Therefore, the light flux reflected by the reflection surface exits in a direction right opposite to the entering direction of the light beam L3. The light beam L3 reflected by the reflection surface is refracted by the surface S2 and becomes the light beam L4 that passes through the medium 60. The optical path of the light beam L3 reflected by the reflection surface is the same as the optical path of the light beam L3 before being reflected by the reflection surface. Therefore, the light beam 4 is aligned with the light beam L2.

On the other hand, the light beam L7 enters the reflection member 62 and is reflected by the reflection surface. The light flux reflected by the reflection surface exits in a direction further away from the optical axis. However, the reflection surface of the reflection member 62 has a positive refractive power. Therefore, the degree of separation from the optical axis is smaller than that of the reflection member 61. The light beam L7 reflected by the reflection surface is refracted by the surface S2 and becomes the light beam L8 that passes through the medium 60.

The light beam L6 and the light beam L8 both are light beams intersecting with the optical axis. However, the angle formed by the light beam L8 and the optical axis and the angle formed by the light beam L6 and the optical axis are not greatly different from each other. Therefore, although the light beam L6 and the light beam L8 are not aligned with each other, the difference thereof is very small.

Moreover, when the differences between θ1 and θ2 are compared, the difference is smaller in a case in which the reflection member has a positive refractive power than in a case in which the reflection member has a flat surface. θ1 and θ2 are angles formed by the light beam exiting from the surface S1 and the optical axis.

In this way, in the specimen observation apparatus of the present embodiment, the illumination light reflected by the reflection member travels to the specimen S with the width that is the same as that at the time of entering the reflection member. Therefore, the illumination efficiency does not decrease.

Moreover, it is possible to reduce the angular variation between the light beam near the optical axis and the light beam far away from the optical axis. Therefore, the optical path entering the reflection member and the optical path after the reflection can be made closer to an aligned state for both on the optical axis and out of the optical axis.

Figure 11:
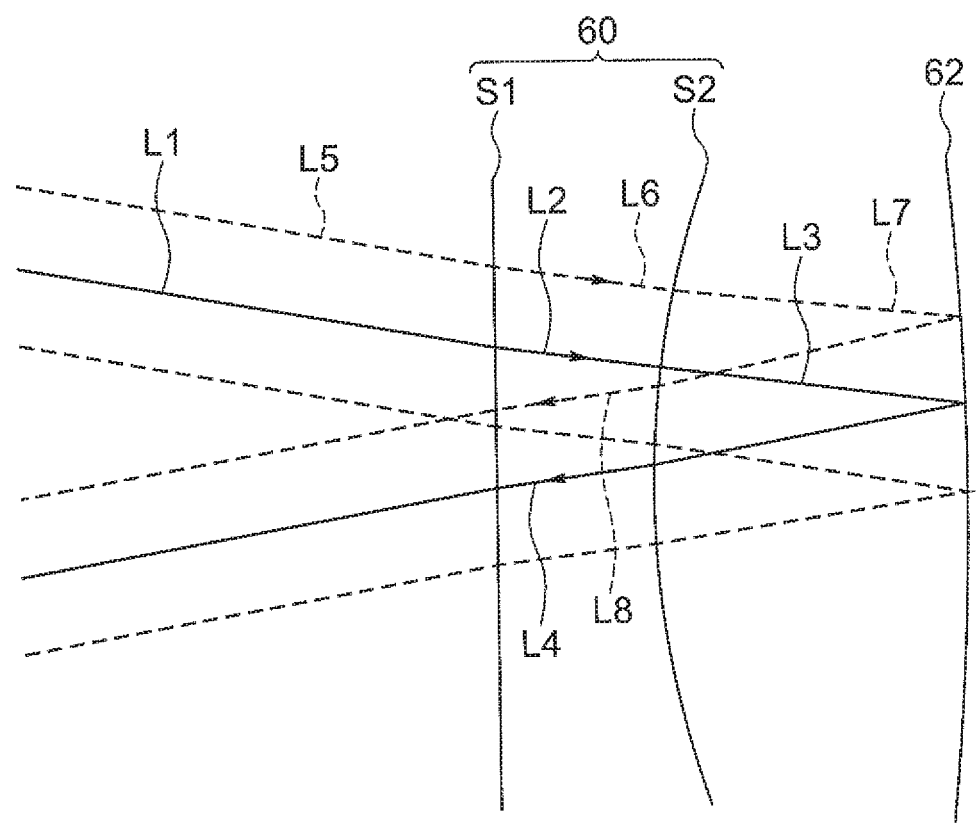
FIG. 11 is a diagram illustrating a manner of light beams in another illumination method and is a diagram illustrating a manner of light beams passing through the culture medium from the objective lens side and light beams passing through the culture medium from the reflection member side.

When the microplate 50 is illuminated by the illumination method illustrated in FIG. 7, it is also preferred that the reflection member have a positive refractive power. FIG. 11 is a diagram illustrating a manner of light beams in another illumination method and a diagram of a manner of light beams passing through the medium from the objective lens side and light beams passing through the medium from the reflection member side.

As illustrated in FIG. 11, the light beam L1 and the light beam L5 are light beams entering the medium 60 from the objective lens side and are light beams intersecting with the optical axis. The surface S1 is a flat surface, but the light beam L1 and the light beam L5 do not vertically enter the surface S1. Therefore, the light beam L1 and the light beam L5 are refracted by the surface S1 and enter the inside of the medium 60. The light beam L2 and the light beam L6 passing through the medium 60 also are light beams intersecting with the optical axis.

The light beam L2 and the light beam L6 pass through the surface S2 and exit from the medium 60. Since the surface S2 is a concave surface, the light beam L2 and the light beam L6 are refracted by the surface S2. The light beam L3 and the light beam L7 exit from the medium 60. At this time, the light beam L7 travels in a direction away from the light beam L3. That is, the parallel light flux that has entered the surface S1 exits from the surface S2 as a divergent light flux.

The light beam L3 and the light beam L7 enter the reflection member 62 and are reflected by the reflection surface of the reflection member 62. The light beam L3 and the light beam L7 reflected by the reflection surface are refracted by the surface S2 and become the light beam L4 and the light beam L8 that pass through the medium 60.

Here, the reflection surface of the reflection member 62 has a positive refractive power. Therefore, the degree of divergence of the divergent light flux that has entered the reflection surface is reduced as a result of the convergence effect of the reflection surface. Therefore, the absolute value of the angle formed by the light beam L2 and the optical axis and the absolute value of the angle formed by the light beam L4 and the optical axis are approximately the same. The same applies to the light beam L6 and the light beam L8.

In this way, by making the reflection member to have a positive refractive power, also in another illumination method, the illumination light reflected by the reflection member travels to the specimen S with the width that is the same as that at the time of entering the reflection member. Therefore, the illumination efficiency does not decrease.

Moreover, in the specimen observation apparatus of the present embodiment, it is preferred that the reflectance of the reflection member be 50% or more.

By doing this, an image having a high contrast can be obtained.

Moreover, in the specimen observation apparatus of the present embodiment, it is preferred that the reflection member have a reflection angle limiting structure configured to make the numerical aperture of the illumination light after the reflection smaller than the numerical aperture of the entering illumination light.

By doing this, the numerical aperture of the illumination light can be limited. Therefore, the image having a high contrast can be obtained. Moreover, since stray light can also be prevented, the image having a high contrast can be obtained.

Moreover, when a microplate is used as the container 10, the liquid surface has a concave shape. The height of the liquid surface is higher at the edge of the well than at the center. Thus, when the reflection angle limiting structure is provided with a feature that limits the numerical aperture of the illumination light applied to this edge, the edge of the well becomes easier to be seen.

For example, a louver film is an element having the reflection angle limiting structure. In the louver film, a light transmission layer and a light shielding layer are alternately laminated. Such a louver film may be applied on the reflection member.

Moreover, in the specimen observation apparatus of the present embodiment, it is preferred that the following Conditional Expression (4) be satisfied:

$$0.01 < NA_{ill}/NA_{ob} < 1 \tag{4}$$

where $NA_{ill}$ is the numerical aperture of the illumination optical system on the specimen side; and $NA_{ob}$ is the numerical aperture of the imaging optical system on the specimen side.

By satisfying Conditional Expression (4), the colorless and transparent specimen can be observed more clearly even in the state of bright-field observation.

In a case of falling below a lower limit value of Conditional Expression (4), the numerical aperture of the illumination optical system on the specimen side becomes excessively small. In this case, light amount insufficiency and illumination unevenness of the illumination light are increased. Furthermore, in the electronic image, dirt or dust on a cover glass stands out.

In a case of exceeding an upper limit value of Conditional Expression (4), the numerical aperture of the illumination optical system on the specimen side becomes excessively large. In this case, incident illumination light oblique with respect to the optical axis increases. Therefore, it is difficult to obtain an electronic image having a satisfactory contrast.

It is preferred that the following Conditional Expression (4') be satisfied instead of Conditional Expression (4).

$$0.02 < NA_{ill}/NA_{ob} < 0.9 \quad (4')$$

It is further preferred that the following Conditional Expression (4'') be satisfied instead of Conditional Expression (4).

$$0.03 < NA_{ill}/NA_{ob} < 0.8 \quad (4'')$$

Moreover, in the specimen observation apparatus of the present embodiment, it is preferred that the following Conditional Expression (5) be satisfied:

$$0.1 \, \mu m < \Delta Z \times NA_{ob}^2 < 30 \, \mu m \quad (5)$$

where $\Delta Z$ is a difference between the focus position of the imaging optical system and the position of the specimen; and $NA_{ob}$ is the numerical aperture of the imaging optical system on the specimen side.

By satisfying Conditional Expression (5), the colorless and transparent specimen can be observed more clearly even in the state of bright-field observation.

Conditional Expression (5), the difference between the focus position of the imaging optical system and the position of the specimen becomes excessively small. In this case, the wavefront aberration amount of the diffracted light is reduced. In particular, the wavefront aberration amount of the first-order diffracted light becomes smaller than λ/4. Therefore, it is difficult to obtain an electronic image having a satisfactory contrast.

In a case of exceeding an upper limit value of Conditional Expression (5), the difference between the focus position of the imaging optical system and the position of the specimen becomes excessively large. In this case, the wavefront aberration amount of the diffracted light becomes larger. In particular, the wavefront aberration amount of the first-order diffracted light becomes larger than λ/4. Moreover, the optical image becomes greatly blurred. As a result, it is difficult to obtain an electronic image having high resolution.

It is preferred that the following Conditional Expression (5') be satisfied instead of Conditional Expression (5).

$$0.2 \, \mu m < \Delta Z \times NA_{ob}^2 < 25 \, \mu m \quad (5')$$

It is further preferred that the following Conditional Expression (5'') be satisfied instead of Conditional Expression (5).

$$0.3 \, \mu m < \Delta Z \times NA_{ob}^2 < 20 \, \mu m \quad (5'')$$

Moreover, in the specimen observation apparatus of the present embodiment, it is preferred that the following Conditional Expression (6) be satisfied:

$$0.05 \, \mu m < \Delta Z \times NA_{ill} < 10 \, \mu m \quad (6)$$

where $\Delta Z$ is the difference between the focus position of the imaging optical system and the position of the specimen; and $NA_{ill}$ is the numerical aperture of the illumination optical system on the specimen side.

By satisfying Conditional Expression (6), the colorless and transparent specimen can be observed more clearly even in the state of bright-field observation.

In a case of falling below the lower limit value of Conditional Expression (6), the difference between the focus position of the imaging optical system and the position of the specimen becomes excessively small. In this case, the wavefront aberration amount of the diffracted light becomes smaller. In particular, the wavefront aberration amount of the first-order diffracted light becomes smaller than λ/4. Therefore, it is difficult to obtain the electronic image having a satisfactory contrast.

In a case of exceeding an upper limit value of Conditional Expression (6), the difference between the focus position of the imaging optical system and the position of the specimen becomes excessively large. In this case, the wavefront aberration amount of the diffracted light becomes larger. In particular, the wavefront aberration amount of the first-order diffracted light becomes larger than λ/4. Moreover, the optical image becomes greatly blurred. As a result, it is difficult to obtain an electronic image having high resolution. Moreover, in a case of exceeding the upper limit value of Conditional Expression (6), the numerical aperture of the illumination optical system on the specimen side becomes excessively large. In this case, incident illumination light oblique with respect to the optical axis is increased. Therefore, it is difficult to obtain the electronic image having a satisfactory contrast.

It is preferred that the following Conditional Expression (6') be satisfied instead of Conditional Expression (6).

$$0.1 \, \mu m < \Delta Z \times NA_{ill} < 8 \, \mu m \quad (6')$$

It is further preferred that the following Conditional Expression (6'') be satisfied instead of Conditional Expression (6).

$$0.2 \, \mu m < \Delta Z \times NA_{ill} < 6 \, \mu m \quad (6'')$$

Moreover, in the specimen observation apparatus of the present embodiment, it is preferred that the illumination light be monochromatic light.

By doing this, the occurrence of chromatic aberration in the imaging optical system can be reduced. Therefore, the image having a high contrast can be obtained.

Moreover, it is preferred that the specimen observation apparatus of the present embodiment include a plurality of imaging optical systems.

Figure 12:
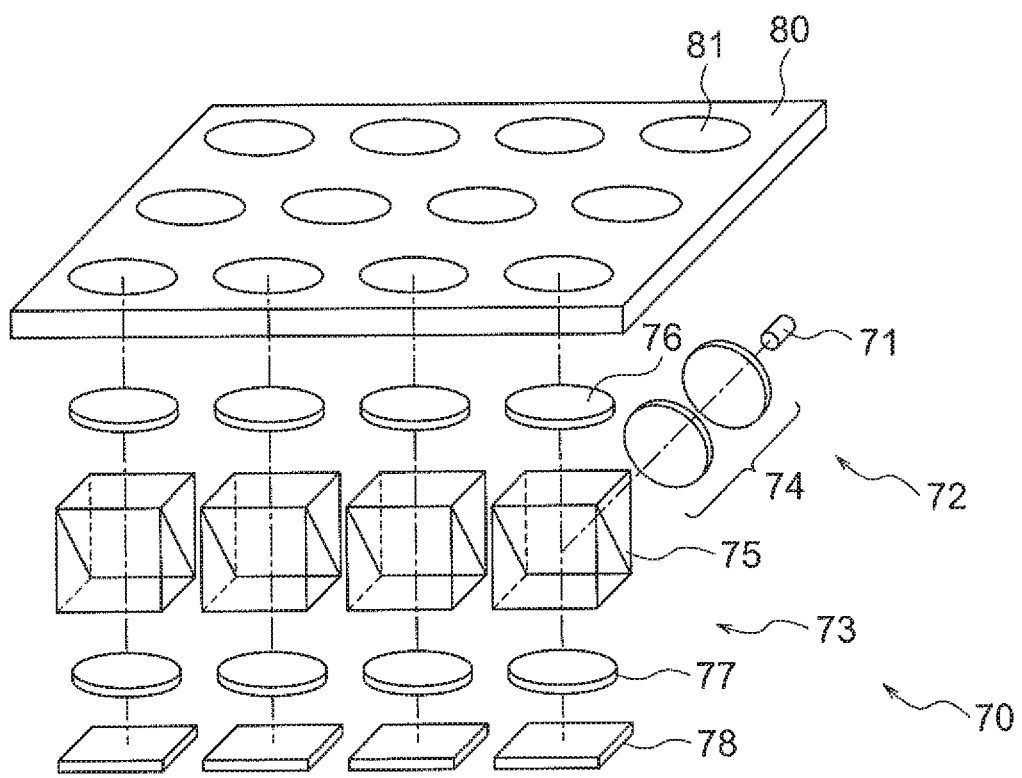
FIG. 12 is a diagram illustrating a specimen observation apparatus including a plurality of imaging optical systems.

FIG. 12 is a diagram illustrating a specimen observation apparatus including a plurality of imaging optical systems. A specimen observation apparatus 70 includes a plurality of observation units each including an imaging optical system. One observation unit includes a light source 71, an illumination optical system 72, and an imaging optical system 73. The illumination optical system 72 includes a light collecting optical system 74, a half prism 75, and an objective lens 76. The imaging optical system 73 includes the objective lens 76, the half prism 75, and a tube lens 77. The observation unit further includes an image pickup device 78.

The number of the observation units is equal to the number of wells 81 included in one row in a microplate 80. In FIG. 12, since the number of the wells 81 included in one row is four, the number of the observation units is also four. Moreover, the observation units are disposed in one row as the arrangement of the wells 81.

In the specimen observation apparatus 70, all the wells 81 can be observed by moving the observation unit in a direction perpendicular to the arrangement direction of the observation units. In FIG. 12, the reflection member is disposed on the microplate 80 although the reflection member is not shown. Therefore, also in the specimen observation apparatus 70, the optical image having a contrast is formed by forming the optical image in the state in which the position of the specimen S and the focus position are different from each other.

Moreover, a specimen observation method of the present embodiment includes an acquisition step of acquiring an electronic image of a specimen and a subtraction step of subtracting a direct current component (DC component) from a signal of the electronic image. The acquisition step is performed in the state of bright-field observation and the state in which the illumination light that is transmitted through the specimen is applied to the specimen again. The electronic image in the subtraction step is an image acquired in a predetermined state. In the predetermined state, the position of the specimen and the focus position of the imaging optical system are different from each other and the focus position is a position at which the phases of the zero-order diffracted light and the first-order diffracted light at a spatial frequency of the specimen at a position of an image point on an optical axis are the same.

Figure 13:
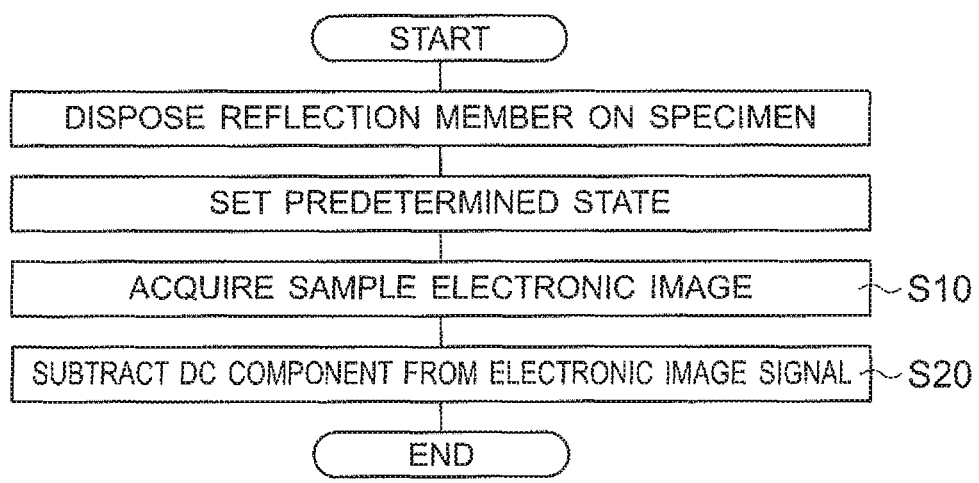
FIG. 13 is a flowchart of a specimen observation method of the first embodiment.

A specimen observation method of the first embodiment is described with reference to FIG. 13. FIG. 13 is a flowchart of the specimen observation method of the first embodiment.

The specimen observation method of the first embodiment includes an acquisition step S10 and a subtraction step S20. As a result, a clear electronic image is obtained in the specimen observation method of the first embodiment.

In the specimen observation method of the first embodiment, a preparation needed for the observation is performed before the execution of the acquisition step S10. In this preparation, the reflection member is disposed above the specimen. The reflection member may be disposed as illustrated in FIG. 5 and FIG. 6.

The predetermined state is set after the disposition of the reflection member is finished. The predetermined state is a state in which the position of the specimen and the focus position of the imaging optical system are different from each other. The focus position is a position at which the phases of the zero-order diffracted light and the first-order diffracted light at the spatial frequency of the specimen are the same.

After the predetermined state is set, the acquisition step S10 is executed. In the acquisition step S10, acquisition of the electronic image of the specimen (hereinafter referred to as "electronic image") is performed. The image of the specimen (optical image) is formed by the imaging optical system. In the acquisition of the electronic image, the image is picked up by an image pickup element such as a CCD and a CMOS. As a result of the image pickup, the image of the specimen is converted to an electronic image (digital data). Since the image of the specimen is formed in the state of bright-field observation, the electronic image is also obtained in the state of bright-field observation.

When the acquisition step S10 ends, the subtraction step S20 then is executed. At the subtraction step S20, a DC component (bias component) is subtracted from a signal of the electronic image.

As stated above, at the acquisition step S10, the sample position and the in-focus position are different. Therefore, $2A_1A_2 \cos \psi \neq 0$ holds. In this case, the intensity I of light at the image plane can be represented by the following expression:

$$I = A_1^2 + A_2^2 + 2A_1A_2 \cos \psi.$$

Here, $A_1^2 + A_2^2$ represents the DC component (bias component) at the image of the sample, i.e., the DC component (bias component) of a signal of the electronic image. Among them, the amplitude $A_1^2$ of the zero-order diffracted light has a very large value. Therefore, at the subtraction step S20, the value of $A_1^2$ is made smaller. By doing so, it is possible to make the value of $2A_1A_2 \cos \psi$ relatively large with reference to the value of $A_1^2 + A_2^2$. As a result, it is possible to observe the sample S (image of the sample S) clearly.

The electronic image in the subtraction step S20 is an image acquired in the predetermined state. In the predetermined state, since at least the position of the specimen and the focus position are different from each other, electronic image having a contrast is obtained in this state. The contrast can be enhanced by executing the subtraction step S20.

As described above, according to the specimen observation method of the first embodiment, the colorless and transparent specimen can be clearly observed without limitation in thickness thereof even in the state of bright-field observation.

Moreover, it is preferred that the specimen observation method of the present embodiment include an amplification step after the subtraction step and the signal of the electronic image after the subtraction step be amplified in the amplification step.

Figure 14:
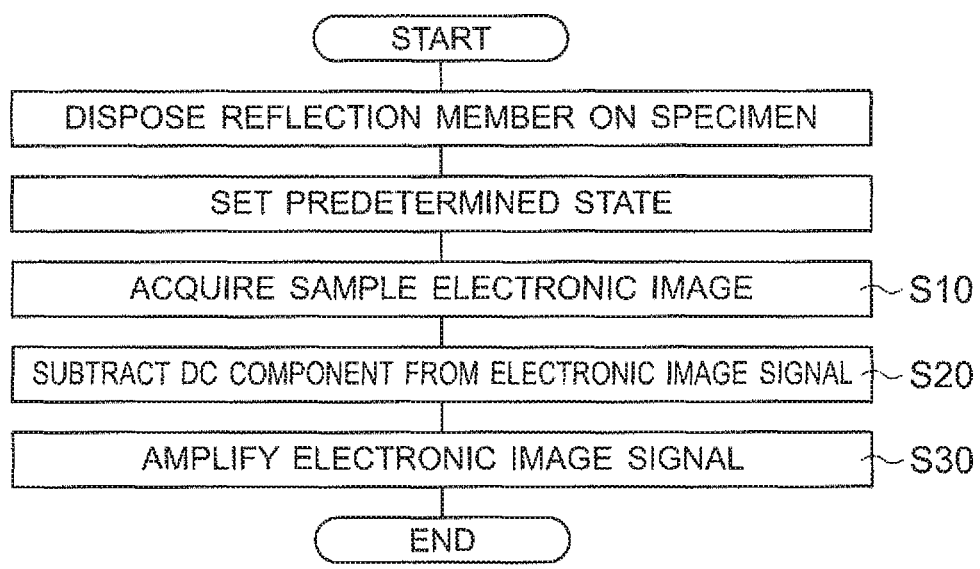
FIG. 14 is a flowchart of a specimen observation method of the second embodiment.

A specimen observation method of the second embodiment is described with reference to FIG. 14. FIG. 14 is a flowchart of the specimen observation method of the second embodiment.

As illustrated in FIG. 14, the specimen observation method of the second embodiment includes an amplification step S30 in addition to the acquisition step S10 and the subtraction step S20. As a result, a clearer electronic image is obtained in the specimen observation method of the second embodiment.

As described above, $A_1^2 + A_2^2$ represents the DC component of the sample image, i.e., the DC component of a signal of the electronic image. At the subtraction step S20, the value of $A_1^2$ is made smaller, whereby the value of $2A_1A_2 \cos \psi$ is made relatively large with reference to the value of $A_1^2 + A_2^2$.

Whereas, in the sample observation method of the second embodiment, the amplification step S30 is executed after the acquisition step S10 and the subtraction step S20 end. At the amplification step S30, the value of $2A_1A_2 \cos \psi$ is made larger (amplified). By doing so, it is possible to make the value of $2A_1A_2 \cos \psi$ relatively large with reference to the value of $A_1^2 + A_2^2$. As a result, it is possible to observe the sample S (image of the sample S) more clearly.

Moreover, it is preferred that the specimen observation method of the present embodiment include a step of calculating the phase amount.

Figure 15:
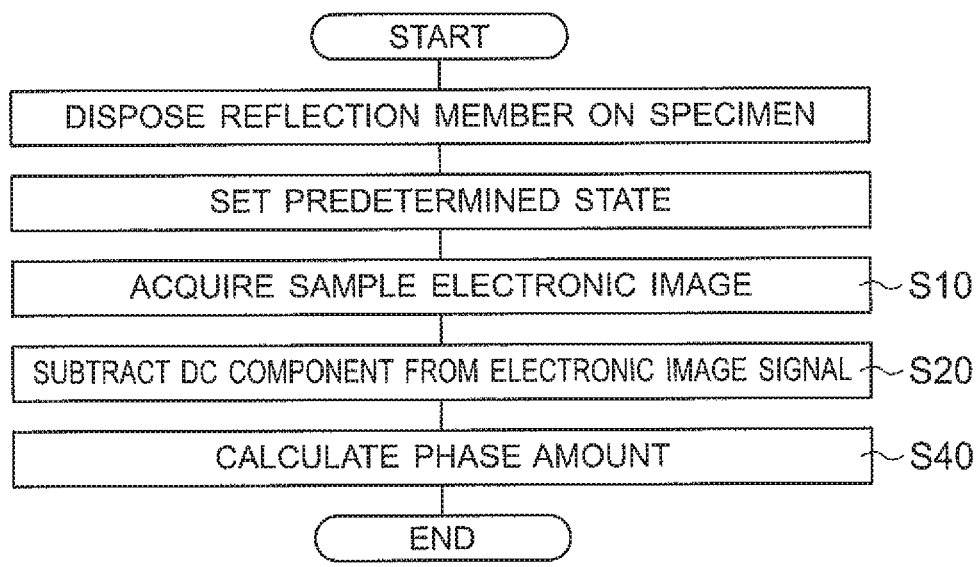
FIG. 15 is a flowchart of a specimen observation method of a third embodiment.

A specimen observation method of a third embodiment is described with reference to FIG. 15. FIG. 15 is a flowchart of the specimen observation method of the third embodiment.

As illustrated in FIG. 15, the specimen observation method of the third embodiment includes Step S40 for calculating the phase amount in addition to the acquisition step S10 and the subtraction step S20. As a result, in the specimen observation method of the third embodiment, the phase amount in the specimen can be determined.

Moreover, it is preferred that the specimen observation method of the present embodiment include a step of acquiring an electronic image for correction, the electronic image for correction be an electronic image acquired in a state in which no specimen exists in the container, and the signal of the electronic image for correction be subtracted from the signal of the electronic image of the specimen in the subtraction step.

A specimen observation method of a fourth embodiment is described with reference to FIG. 16. FIG. 16 is a flowchart of the specimen observation method of the fourth embodiment.

As illustrated in FIG. 16, the specimen observation method of the fourth embodiment includes Step S50 for acquiring an electronic image for correction and Step S50 for subtracting the electronic image for correction from the electronic image in addition to the acquisition step S10 and the subtraction step S20.

In the specimen observation method of the fourth embodiment, Step S50 for acquiring the electronic image for correction is executed before the reflection member is disposed on the specimen. In Step S50, the reflection member is not disposed on the specimen. In this case, since a large portion of the illumination light just passes through the specimen, a large portion of the illumination light does not enter the imaging optical system again. However, since part of the illumination light is reflected by a bottom surface of the container, the reflected light from the bottom surface of the container enters the imaging optical system.

Since the reflected light from the bottom surface of the container is light without information on the specimen, the reflected light from the bottom surface of the container is unnecessary light. Since the reflected light from the bottom surface of the container is generated also when the reflection member is disposed on the specimen, the reflected light from the bottom surface of the container is superimposed on the image of the specimen as a background when the specimen is observed. As described above, since the reflected light from the bottom surface of the container is unnecessary light, it is preferred to remove the reflected light from the bottom surface of the container.

Thus, Step S50 is executed. In this case, the optical image is formed by only the reflected light from the bottom surface of the container. Thus, an electronic image is acquired by picking up this optical image, and the acquired electronic image is made to be the electronic image for correction.

As described above, the reflected light from the bottom surface of the container is superimposed on the image of the specimen as a background. Thus, Step S60 is executed. In Step S60, the electronic image for correction is subtracted from the electronic image of the specimen. By doing this, since the signal of the electronic image for correction is subtracted from the signal of the electronic image of the specimen, the background superimposed on the image of the specimen can be removed. As a result, the specimen (the image of the specimen) can be observed more clearly. Moreover, when the phase amount is determined, the phase amount can be determined with more precision.

Moreover, it is preferred that the specimen observation method of the present embodiment include a step of measuring the number of cells.

By doing this, it is possible to measure the number and the density of the cells.

Moreover, in the specimen observation apparatus and specimen observation method of the present embodiment, a specimen storage unit may be used which includes a container and a protection member. The protection member is located above the container, and the protection member includes a reflection region in a region opposed to a recessed portion of the container.

Figure 17A:
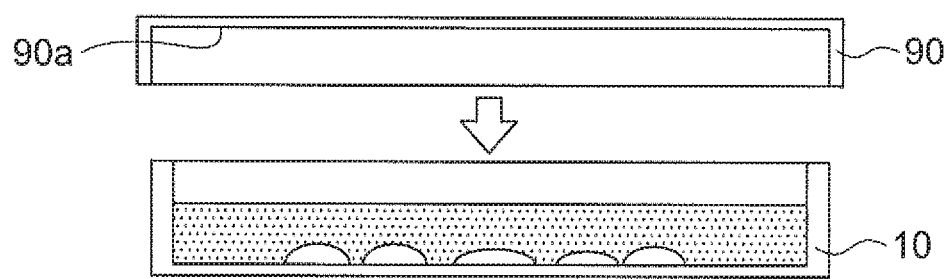
FIG. 17A is a diagram illustrating a case in which a specimen storage portion including a reflection region is a petri dish.
Figure 17B:
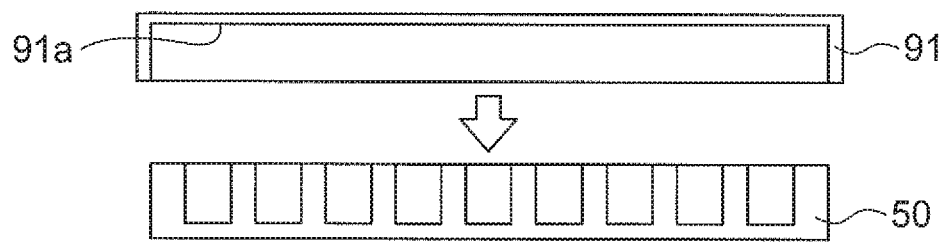
FIG. 17B is a diagram illustrating a case in which the specimen storage portion including the reflection region is a microplate.

FIG. 17A is a diagram illustrating an example of the specimen storage unit including the reflection region in which the container is a petri dish. FIG. 17B is a diagram illustrating an example of the specimen storage unit including the reflection region in which the container is a microplate.

As illustrated in FIG. 17A, the specimen storage unit includes a petri dish as a container 10 and a protection member 90. The protection member 90 is a lid and is located above the container 10. Then, a reflection region 90a is formed on the inner side of the protection member 90. When using the specimen storage unit shown in FIG. 17A, the reflecting member 6 shown in FIG. 1 may be omitted since the reflection region 90a works as a substitute of the reflecting member.

Moreover, as illustrated in FIG. 17B, the specimen storage unit includes a microplate as a container 50 and a protection member 91. The protection member 91 is a lid and is located above the container 50. Then, a reflection region 91a is formed on the inner side of the protection member 91. When using the specimen storage unit shown in FIG. 17B, the reflecting member 6 shown in FIG. 1 may be omitted since the reflection region 91a works as a substitute of the reflecting member.

Moreover, in the specimen storage unit, it is preferred that the reflectance of the surface on the imaging optical system side be 8% or less.

When observation of a specimen is performed with the specimen observation apparatus of the present embodiment by using the specimen storage unit, the petri dish 10 or the microplate 50 is placed on the stage 4. In this case, the bottom surface of the petri dish or the bottom surface of the microplate is located on the opening portion in the stage 4. That is, the bottom surface of the petri dish or the bottom surface of the microplate is opposed to the imaging optical system 5 side.

Since the illumination light is applied to the specimen S through the opening portion in the stage 4, the illumination light is applied to the bottom surface of the petri dish or the bottom surface of the microplate. At this time, most of the illumination light is transmitted through the bottom surface of the petri dish or the bottom surface of the microplate.

However, part of the illumination light is reflected by the bottom surface of the petri dish or the bottom surface of the microplate. The reflected light is superimposed on the image of the specimen S. Therefore, the contrast of the image of the specimen S decreases when the light amount of the reflected light is high.

Thus, by setting the reflectance of the surface of the specimen storage unit on the imaging optical system side to be 8% or less, the decrease in the contrast of the image of the specimen S can be prevented.

Moreover, it is preferred that the specimen observation apparatus satisfy the following Conditional Expression (7) when the liquid stored in the container is considered as a lens and the reflection member or the reflection region is formed in a concave shape:

$$0.7 < (|f_1|+x)/f_2 < 1.4 \qquad (7)$$

where $f_1$ is a focal length of the lens when the liquid stored in a recessed portion of the container is considered as the lens;

$f_2$ is a focal length of the reflection surface of the reflection member or the reflection region; and x is a distance from the liquid surface to the reflection surface.

As described above, in the microplate, since the area of the recessed portion is narrow, the liquid surface has a concave shape. Thus, when the liquid part, that is, the medium is considered as the lens, the medium functions as a negative lens. On the other hand, the reflection member serves as a positive lens when the reflection surface is formed on a concave shape.

By satisfying Conditional Expression (7), the illumination light reflected by the reflection member travels to the specimen S with the width that is the same as that at the time of entering the reflection member. Therefore, the illumination efficiency does not decrease.

Moreover, the angular variation between the light beam near the optical axis and the light beam far away from the optical axis can be reduced. Therefore, the angles of the reflected illumination light become close to each other over the entire range.

Moreover, when $f_2=|f_1|+x$, the arrangement of the optical system including the medium and the reflection member becomes the arrangement of an afocal optical system. In this case, the light beam has the same angle before and after being reflected by the reflection member. Therefore, the optical path entering the reflection member and the optical path after the reflection can be made closer to an aligned state for both on the optical axis and out of the optical axis.

In the specimen observation apparatus of the present embodiment, it is preferred that the transmittance of the reflection member be 3% or more.

When the reflection member has a light transmitting property as well as the light reflecting property, the transmitted illumination of the sample can be performed through the reflection member. Therefore, a transmitted light observation such as a phase contrast observation can be performed by using such transmitted illumination.

In the specimen observation apparatus of the present embodiment, it is preferred that wavelength for the maximum transmittance and wavelength for the maximum reflectance of the reflection member are different from each other.

By doing this, for example, the specimen observation can be performed in the specimen observation apparatus of the present embodiment with use of the light having a wavelength bandwidth corresponding to a large reflectance of the reflection member and the phase contrast observation can be performed with use of the light having a wavelength bandwidth corresponding to a large transmittance.

Various modifications can be adopted in the present invention without departing from the gist of the present invention.

As described above, the present invention is suitable for the compact specimen observation apparatus in which the colorless and transparent specimen can be observed without limitation in thickness thereof even in the state of brightfield observation. Furthermore, the present invention is suitable for the specimen observation method in which the colorless and transparent specimen can be observed without limitation in thickness thereof even in the state of brightfield observation.

What is claimed is:

1. A specimen observation apparatus comprising:
   a light source;
   an illumination optical system;
   a stage on which a specimen is able to be disposed;
   an imaging optical system; and
   a reflection member disposed at a position opposed to the imaging optical system across the stage,
   wherein:
   the illumination optical system is disposed so as to apply illumination light from the light source to the specimen,
   the imaging optical system is disposed at a position at which the illumination light that is transmitted through the specimen and thereafter reflected by the reflection member to be transmitted through the specimen again enters, and is configured to form an optical image of the specimen,
   the optical image is formed in a state in which a position of the specimen and a focus position of the imaging optical system are different from each other,
   the focus position is a position at which phases of zero-order diffracted light and first-order diffracted light at a spatial frequency of the specimen at a position of an image point on an optical axis are the same, and
   the following Conditional Expression (1) is satisfied:

$$10 \le D \times NA_{ob}^2/\lambda \le 10000 \qquad (1)$$

where
   D is a distance (mm) between the position of the specimen and a reflection surface of the reflection member,
   $NA_{ob}$ is a numerical aperture of the imaging optical system on the specimen side, and
   $\lambda$ is a center wavelength (mm) of a wavelength range of the illumination light.

2. The specimen observation apparatus according to claim 1, further comprising:
   an image pickup device; and
   an image processing device,
   wherein:
   the image pickup device is disposed at a position at which the optical image is formed, and
   the image processing device generates an observation image signal from an optical image obtained in a state in which the position of the specimen and the focus position of the imaging optical system are different from each other.

3. The specimen observation apparatus according to claim 1, wherein the following Conditional Expression (2) is satisfied:

$$4 \times NA_{ill} \times D + A < L \qquad (2)$$

where
   $NA_{ill}$ is a numerical aperture of the illumination optical system on the specimen side,
   A is a diameter (mm) of an observation field of view at the position of the specimen,
   L is a diameter (mm) of an illumination range of the illumination optical system at the position of the specimen, and
   the diameter of the observation field of view and the diameter of the illumination range are diameters in a state in which the position of the specimen and the focus position of the imaging optical system are different from each other.

4. The specimen observation apparatus according to claim 1, wherein the reflection member is disposed at a position different from a position conjugate to a pupil of the imaging optical system.

5. The specimen observation apparatus according to claim 1, wherein the reflection member has a positive refractive power.

6. The specimen observation apparatus according to claim 1, wherein a reflectance of the reflection member is at least 50%.

7. The specimen observation apparatus according to claim 1, wherein the reflection member has a reflection angle limiting structure configured to make a numerical aperture of illumination light after reflection smaller than a numerical aperture of entering illumination light.

8. The specimen observation apparatus according to claim 1, wherein the following Conditional Expression (4) is satisfied:

$$0.01 < NA_{ill}/NA_{ob} < 1 \qquad (4)$$

where
$NA_{ill}$ is a numerical aperture of the illumination optical system on the specimen side.

9. The specimen observation apparatus according to claim 1, wherein the following Conditional Expression (5) is satisfied:

$$0.1 \ \mu m < \Delta Z \times NA_{ob}^2 < 30 \ \mu m \qquad (5)$$

where
$\Delta Z$ is a difference between the focus position of the imaging optical system and the position of the specimen.

10. The specimen observation apparatus according to claim 1, wherein the following Conditional Expression (6) is satisfied:

$$0.05 \ \mu m < \Delta Z \times NA_{ill} < 10 \ \mu m \qquad (6)$$

where
$\Delta Z$ is a difference between the focus position of the imaging optical system and the position of the specimen, and
$NA_{ill}$ is a numerical aperture of the illumination optical system on the specimen side.

11. The specimen observation apparatus according to claim 1, wherein the illumination light is monochromatic light.

12. The specimen observation apparatus according to claim 1, further comprising a plurality of the imaging optical systems.

13. A specimen observation method comprising:
an acquisition step of acquiring an electronic image of a specimen; and
a subtraction step of subtracting a direct current component from a signal of the electronic image,
wherein:
the acquisition step is performed in a state of bright-field observation and a state in which illumination light that is transmitted through the specimen is reflected by a reflection member and is applied to the specimen again,
the electronic image at the subtraction step is an image acquired in a predetermined state,
in the predetermined state, a position of the specimen and a focus position of an imaging optical system are different from each other,
the focus position is a position at which phases of zero-order diffracted light and first-order diffracted light at a spatial frequency of the specimen at a position of an image point on an optical axis are the same, and
the following Conditional Expression (1) is satisfied:

$$10 \leq D \times NA_{ob}^2/\lambda \leq 10000 \qquad (1)$$

where
D is a distance (mm) between the position of the specimen and a reflection surface of the reflection member,
$NA_{ob}$ is a numerical aperture of the imaging optical system on the specimen side, and
$\lambda$ is a center wavelength (mm) of a wavelength range of the illumination light.

14. The specimen observation method according to claim 13, further comprising an amplification step after the subtraction step,
wherein a signal of an electronic image after the subtraction step is amplified in the amplification step.

15. The specimen observation method according to claim 13, further comprising a step of calculating a phase amount.

16. The specimen observation method according to claim 13, further comprising a step of acquiring an electronic image for correction,
wherein the electronic image for correction is an electronic image acquired in a state in which no specimen exists in a specimen container, and
the signal of the electronic image for correction is subtracted from the signal of the electronic image of the specimen in the subtraction step.

17. A specimen observation apparatus comprising:
a light source;
an illumination optical system;
a stage on which a specimen is able to be disposed;
an imaging optical system; and
a reflection member disposed at a position opposed to the imaging optical system across the stage,
wherein:
the illumination optical system is disposed so as to apply illumination light from the light source to the specimen,
the imaging optical system is disposed at a position at which the illumination light that is transmitted through the specimen and thereafter reflected by the reflection member to be transmitted through the specimen again enters, and is configured to form an optical image of the specimen,
the optical image is formed in a state in which a position of the specimen and a focus position of the imaging optical system are different from each other,
the focus position is a position at which phases of zero-order diffracted light and first-order diffracted light at a spatial frequency of the specimen at a position of an image point on an optical axis are the same, and
the following Conditional Expression (2) is satisfied:

$$4 \times NA_{ill} \times D + A < L \qquad (2)$$

where
$NA_{ill}$ is a numerical aperture of the illumination optical system on the specimen side,
D is a distance (mm) between the position of the specimen and a reflection surface of the reflection member,
A is a diameter (mm) of an observation field of view at the position of the specimen,
L is a diameter (mm) of an illumination range of the illumination optical system at the position of the specimen, and
the diameter of the observation field of view and the diameter of the illumination range are diameters in a state in which the position of the specimen and the focus position of the imaging optical system are different from each other.

18. A specimen observation method comprising:
an acquisition step of acquiring an electronic image of a specimen; and
a subtraction step of subtracting a direct current component from a signal of the electronic image,
wherein:
the acquisition step is performed in a state of bright-field observation and a state in which illumination light that is transmitted through the specimen is reflected by a reflection member and is applied to the specimen again,
the electronic image at the subtraction step is an image acquired in a predetermined state, in the predetermined state, a position of the specimen and a focus position of an imaging optical system are different from each other, the focus position is a position at which phases of zero-order diffracted light and first-order diffracted light at a spatial frequency of the specimen at a position of an image point on an optical axis are the same, and the following Conditional Expression (2) is satisfied:

$$4 \times NA_{ill} \times D + A < L \quad (2)$$

where $NA_{ill}$ is a numerical aperture of the illumination optical system on the specimen side, D is a distance (mm) between the position of the specimen and a reflection surface of the reflection member, A is a diameter (mm) of an observation field of view at the position of the specimen, L is a diameter (mm) of an illumination range of the illumination optical system at the position of the specimen, and the diameter of the observation field of view and the diameter of the illumination range are diameters in a state in which the position of the specimen and the focus position of the imaging optical system are different from each other.

\* \* \* \* \*